(12) United States Patent
Malinskiy et al.

(10) Patent No.: US 11,330,963 B2
(45) Date of Patent: May 17, 2022

(54) WIRELESS MEDICAL IMAGING SYSTEM

(71) Applicant: Lazurite Holdings LLC, Cleveland, OH (US)

(72) Inventors: Eugene Malinskiy, Mayfield Village, OH (US); Ilya Malinskiy, Cleveland Heights, OH (US); Daniel Dudley, Cleveland, OH (US); Howard Fein, Richmond Heights, OH (US); Brad Roskoph, Cleveland, OH (US)

(73) Assignee: Lazurite Holdings LLC, Cleveland, OH (US)

( * ) Notice: Subject to any disclaimer, the term of this patent is extended or adjusted under 35 U.S.C. 154(b) by 0 days.

(21) Appl. No.: 15/776,207

(22) PCT Filed: Nov. 16, 2016

(86) PCT No.: PCT/US2016/062157
§ 371 (c)(1),
(2) Date: May 15, 2018

(87) PCT Pub. No.: WO2017/087448
PCT Pub. Date: May 26, 2017

(65) Prior Publication Data
US 2019/0167074 A1 Jun. 6, 2019

Related U.S. Application Data

(60) Provisional application No. 62/255,825, filed on Nov. 16, 2015.

(51) Int. Cl.
*A61B 1/04* (2006.01)
*A61B 1/06* (2006.01)
(Continued)

(52) U.S. Cl.
CPC ...... *A61B 1/00016* (2013.01); *A61B 1/00032* (2013.01); *A61B 1/00039* (2013.01);
(Continued)

(58) Field of Classification Search
CPC ... A61B 1/00016; A61B 1/042; A61B 1/0669; A61B 1/0638; A61B 1/00039; A61B 1/0646; A61B 1/0653
(Continued)

(56) References Cited

U.S. PATENT DOCUMENTS 5,178,616 A 1/1993 Uemiya et al.
5,311,859 A * 5/1994 Monroe ................. A61B 1/042
348/75
(Continued)

FOREIGN PATENT DOCUMENTS

CN 101821866 A 9/2010
CN 104603530 A 6/2015
(Continued)

OTHER PUBLICATIONS

Extended European Search Report dated Jan. 29, 2019 for European Patent Application No. 16837714.1, 8 pages.
(Continued)

*Primary Examiner* — Matthew J Kasztejna
(74) *Attorney, Agent, or Firm* — Morgan, Lewis & Bockius LLP

(57) ABSTRACT

A wireless medical imaging system comprising a head unit is provided. The head unit comprises a head unit case, an integrated light source, an image sensor, a wireless transceiver, a central processing unit, and a user-input component. The head unit case has an external surface defining an external cavity, an internal surface defining an internal cavity, a first aperture, and a second aperture. The integrated light source, the image sensor, the wireless transceiver, and
(Continued)

the central processing unit are disposed within the internal cavity. The integrated light source extends from within the internal cavity into the first aperture and is configured to transmit light from the head unit through the first aperture. The image sensor is configured to detect an image transmitted into the head unit through the second aperture. The external cavity is configured to receive an external battery. The user-input component is disposed on the external surface.

42 Claims, 14 Drawing Sheets

(51) Int. Cl.
  *A61B 1/00* (2006.01)
  *G02B 23/24* (2006.01)
(52) U.S. Cl.
  CPC .......... *A61B 1/00108* (2013.01); *A61B 1/042* (2013.01); *A61B 1/0638* (2013.01); *A61B 1/0646* (2013.01); *A61B 1/0653* (2013.01); *A61B 1/0669* (2013.01); *G02B 23/2484* (2013.01)
(58) Field of Classification Search
  USPC ............... 600/131, 136; 356/241.1–241.6
  See application file for complete search history.

(56) References Cited

U.S. PATENT DOCUMENTS

| | | | |
|---|---|---|---|
| 5,879,289 | A | 3/1999 | Yarush et al. |
| 6,007,255 | A | 12/1999 | Krauter |
| 6,043,839 | A | 3/2000 | Adair et al. |
| 6,449,006 | B1 | 9/2002 | Shipp |
| 6,494,826 | B1 * | 12/2002 | Chatenever ........ A61B 1/00188 600/112 |
| 6,806,681 | B1 | 10/2004 | Cheiky |
| 7,091,653 | B2 | 8/2006 | Ouderkirk et al. |
| 7,091,661 | B2 | 8/2006 | Ouderkirk |
| 7,193,248 | B2 | 3/2007 | Weindorf et al. |
| 7,394,188 | B2 | 7/2008 | Ouderkirk et al. |
| 7,442,167 | B2 * | 10/2008 | Dunki-Jacobs ...... A61B 1/0653 600/129 |
| 7,513,669 | B2 | 4/2009 | Chua et al. |
| 7,553,683 | B2 | 6/2009 | Martin et al. |
| 7,668,450 | B2 | 2/2010 | Todd |
| 7,724,412 | B2 | 5/2010 | Powell |
| 7,777,243 | B2 | 8/2010 | Lin et al. |
| 7,786,879 | B2 | 8/2010 | Lax |
| 7,798,692 | B2 | 9/2010 | Krupa |
| 7,837,348 | B2 | 11/2010 | Narendran et al. |
| 7,839,072 | B2 | 11/2010 | Horiuchi et al. |
| 8,029,439 | B2 | 10/2011 | Todd |
| 8,083,364 | B2 | 12/2011 | Allen |
| 8,088,304 | B2 | 1/2012 | Winkler et al. |
| 8,128,557 | B2 * | 3/2012 | Scholly ................. A61B 1/128 600/112 |
| 8,142,051 | B2 | 3/2012 | Ducharme |
| 8,395,312 | B2 | 3/2013 | Hum |
| 8,436,388 | B2 | 5/2013 | Lim et al. |
| 8,519,609 | B2 | 8/2013 | Winkler et al. |
| 8,545,396 | B2 | 10/2013 | Cover et al. |
| 8,558,880 | B2 | 10/2013 | Nambakam et al. |
| 8,562,161 | B2 | 10/2013 | Tong et al. |
| 8,585,273 | B2 | 11/2013 | Pokrovskiy et al. |
| 8,622,893 | B2 * | 1/2014 | Mathieu ................ A61M 39/10 600/132 |
| 8,625,097 | B2 | 1/2014 | Brukilacchio |
| 8,632,196 | B2 | 1/2014 | Tong et al. |
| 8,723,936 | B2 * | 5/2014 | Amling ................. A61B 1/042 348/65 |
| 8,748,921 | B2 | 6/2014 | Martin et al. |
| 8,810,126 | B2 | 8/2014 | Ito |
| 8,827,888 | B2 | 9/2014 | Bolyard |
| 8,841,146 | B2 | 9/2014 | Yen et al. |
| 8,882,284 | B2 | 11/2014 | Tong et al. |
| 8,928,219 | B2 | 1/2015 | Chan et al. |
| 8,946,982 | B2 | 2/2015 | Winkler et al. |
| 9,147,814 | B2 | 9/2015 | Waragaya |
| 9,217,544 | B2 | 12/2015 | Tong et al. |
| 9,217,545 | B2 | 12/2015 | Ito |
| 9,287,469 | B2 | 3/2016 | Chakraborty |
| 9,303,830 | B2 | 4/2016 | Ito |
| 9,316,361 | B2 | 4/2016 | Tong et al. |
| 9,382,472 | B2 | 7/2016 | Hefner, Jr. et al. |
| 9,383,496 | B2 | 7/2016 | Parker et al. |
| 9,404,637 | B2 | 8/2016 | Aeling et al. |
| 9,464,224 | B2 | 10/2016 | Deshpande et al. |
| 9,500,325 | B2 | 11/2016 | Tong et al. |
| 9,551,468 | B2 | 1/2017 | Jones |
| 9,553,230 | B2 | 1/2017 | Yoshida et al. |
| 9,587,791 | B2 | 3/2017 | Ito |
| 9,611,987 | B2 | 4/2017 | Kelchner et al. |
| 9,677,719 | B2 | 6/2017 | He et al. |
| 2002/0120181 | A1 * | 8/2002 | Irion ........................ A61B 1/07 600/178 |
| 2003/0156430 | A1 | 8/2003 | Ota |
| 2005/0006659 | A1 | 1/2005 | Ng et al. |
| 2005/0116635 | A1 | 6/2005 | Ito |
| 2006/0145599 | A1 | 7/2006 | Reza et al. |
| 2006/0171693 | A1 | 8/2006 | Todd et al. |
| 2006/0220613 | A1 | 10/2006 | Abe |
| 2007/0086205 | A1 | 4/2007 | Krupa |
| 2007/0189352 | A1 | 8/2007 | Nagahama et al. |
| 2007/0267967 | A1 | 11/2007 | Soshchin |
| 2008/0183028 | A1 | 7/2008 | Garcia et al. |
| 2008/0262316 | A1 | 10/2008 | Ajima et al. |
| 2009/0034230 | A1 | 2/2009 | Lim et al. |
| 2009/0040523 | A1 | 2/2009 | Brukilacchio |
| 2009/0076328 | A1 | 3/2009 | Root et al. |
| 2009/0151785 | A1 | 6/2009 | Soshchin et al. |
| 2010/0033075 | A1 | 2/2010 | Soshchin et al. |
| 2010/0061077 | A1 | 3/2010 | Winkler et al. |
| 2010/0172148 | A1 | 7/2010 | Komazaki et al. |
| 2010/0298711 | A1 | 11/2010 | Pedersen |
| 2011/0069490 | A1 | 3/2011 | Liu |
| 2011/0157865 | A1 | 6/2011 | Takahashi |
| 2011/0172492 | A1 | 7/2011 | Erikawa |
| 2011/0208004 | A1 | 8/2011 | Feingold |
| 2011/0227102 | A1 | 9/2011 | Hussell et al. |
| 2011/0261183 | A1 | 10/2011 | Ma et al. |
| 2012/0029289 | A1 | 2/2012 | Kucklick |
| 2012/0051075 | A1 | 3/2012 | Harada et al. |
| 2012/0116369 | A1 | 5/2012 | Viola |
| 2013/0027962 | A1 | 1/2013 | Takahashi |
| 2013/0100264 | A1 | 4/2013 | Kazakevich et al. |
| 2013/0139826 | A1 | 6/2013 | Swann et al. |
| 2013/0188383 | A1 | 7/2013 | Jaffe |
| 2013/0314893 | A1 | 11/2013 | Paquette |
| 2013/0324794 | A1 | 12/2013 | Cover et al. |
| 2013/0334546 | A1 | 12/2013 | Wagenblast et al. |
| 2014/0183584 | A1 | 7/2014 | Tong et al. |
| 2014/0221740 | A1 | 8/2014 | Kawula et al. |
| 2014/0275763 | A1 | 9/2014 | King |
| 2014/0320677 | A1 | 10/2014 | Jarvenpaa |
| 2015/0077972 | A1 | 3/2015 | Sugiyama et al. |
| 2015/0115302 | A1 | 4/2015 | Eder et al. |
| 2015/0130935 | A1 | 5/2015 | Siann |
| 2015/0184830 | A1 | 7/2015 | Nagao et al. |
| 2015/0362828 | A1 * | 12/2015 | Patel ...................... G03B 17/48 348/75 |
| 2016/0004147 | A1 | 1/2016 | Hu et al. |
| 2016/0262597 | A1 | 9/2016 | Danchinyu et al. |
| 2017/0003000 | A1 | 1/2017 | Narendran et al. |
| 2017/0045201 | A1 | 2/2017 | Jones |
| 2018/0245775 | A1 | 8/2018 | Malinskiy et al. |

FOREIGN PATENT DOCUMENTS

| | | | |
|---|---|---|---|
| EP | | 2822111 A1 | 1/2015 |
| EP | | 2941175 A1 | 11/2015 |

(56) References Cited

FOREIGN PATENT DOCUMENTS

| | | |
|---|---|---|
| GB | 1542873 A | 3/1979 |
| JP | 10-165362 | 6/1998 |
| JP | 2005-538753 | 12/2005 |
| JP | 2006-61685 | 3/2006 |
| JP | 2006-518939 A | 8/2006 |
| JP | 2006-271697 | 10/2006 |
| JP | 2007-220326 | 8/2007 |
| JP | 2009-195629 | 9/2009 |
| JP | 2010-509990 | 4/2010 |
| JP | 2010-541295 A | 12/2010 |
| JP | 2011-5022 | 1/2011 |
| JP | 2012-533406 | 12/2012 |
| WO | 03082075 | 10/2003 |
| WO | 2004068903 A2 | 8/2004 |
| WO | 2008063565 | 5/2008 |
| WO | 2008087243 A1 | 7/2008 |
| WO | 2009048704 A2 | 4/2009 |
| WO | 2011011234 | 1/2011 |
| WO | 2012016224 A2 | 2/2012 |
| WO | 2012025179 A1 | 3/2012 |
| WO | 2013139619 A1 | 9/2013 |
| WO | 2013139620 A1 | 9/2013 |
| WO | 2013139675 A1 | 9/2013 |
| WO | 2015127630 A1 | 9/2015 |
| WO | 2017031138 A1 | 2/2017 |
| WO | 2017087448 | 5/2017 |
| WO | 2018152196 | 8/2018 |

OTHER PUBLICATIONS

International Search Report and Written Opinion issued in International Application No. PCT/US2016/62157 dated Feb. 3, 2017; 15 pages.
Notice of Reasons for Rejection dated Feb. 5, 2019 for Japanese Patent Application No. 2018-509824, 10 pp.
First Notification of Office Action dated Dec. 26, 2018 for Chinese Patent Application No. 201680048579.6, 5 pp.
Search Report for Chinese Patent Application No. 201680048579.6, 2 pp.
3rd Chinese Office Action dated Apr. 1, 2020 for Chinese Patent Application No. 201680048579.6, 8 pages.
Japanese Office Action dated Jun. 18, 2019 for Japanese Application No. 2018509824, 12 pages.
International Search Report and Written Opinion issued in Application No. PCT/US2016/047235 dated Oct. 28, 2016, 11 pages.
International Search Report and Written Opinion dated Jul. 21, 2020 for International Patent Application No. PCT/US2020/028505, 9 pages.
Supplemental European Search Report dated Oct. 30, 2020 for European Patent Application No. 18753982, 2 pages.
Japanese Office Action dated Jan. 12, 2022 for Japanese Patent Application No. 2020-186909, 21 pages, with English Translation.

* cited by examiner

WIRELESS MEDICAL IMAGING SYSTEM

FIELD OF THE INVENTION

The invention relates to medical imaging systems, and more particularly to wireless medical imaging systems comprising a head unit, the head unit comprising (i) a head unit case, (ii) an integrated light source, (iii) an image sensor, (iv) a wireless transceiver, (v) a central processing unit, and (vi) a user-input component, for use, for example, with endoscopes, arthroscopes, and other surgical optical imaging instruments and systems.

BACKGROUND OF THE INVENTION

Endoscopic surgery involves using a complex optical instrument system in a minimally invasive surgical procedure to visualize the interior of a hollow organ or cavity in a patient's body, such as, for example, inside of a joint, the respiratory tract, the epidural space, etc. Endoscopic procedures are performed for a variety of reasons including diagnostic examination, cauterization, reconstruction, and ligament repair, among others. These procedures can be performed in hospitals, surgical centers, outpatient centers, or physician offices, and are now being adopted for diagnostic field work, including use by the military.

Endoscopic surgery was first developed in the early 1800s and has steadily, but slowly, evolved over time. The first procedures involved using a small tube and lens, i.e. a simple endoscope, inserted into a patient, through which the physician looked while using candlelight for illumination. While these first procedures were revolutionary and significantly expanded medical understanding of the human body, the procedures were fraught with complications and technological limitations.

The need for illumination has been a critical challenge from the inception of endoscopic surgery. Beginning with candles, the light source has presented many difficulties relating to, for example, ease of use, risk of fire, and low light output, among others. As technology advanced, better light sources were introduced, starting with rudimentary electric lights. Although the industry has progressed to modern lighting methods such as xenon and LEDs, these difficulties have persisted.

Another primary challenge for endoscopy has been how physicians visualize the procedure. The first endoscopes were handheld and required a surgeon to have a direct line of sight into and down the length of the scope. While this allowed the surgeon to clearly view the surgical site, it meant that the surgeon was required to maintain a very precise position in order to use the scope. In addition, the need to maintain sight through the scope meant that the surgeon would have a difficult time using the other tools required for effective or complex surgery, as the surgeon would have to manipulate the tools without seeing where the tools were. However, as with light sources, the technology relating to use of scopes has continued to improve, including advances in optical science and adoption of new manufacturing techniques such a fiber optics and precision rod-lenses. Most recently, the advent of inexpensive and accurate image camera sensors have again dramatically shifted the way endoscopic procedures are performed. The use of digital camera and external displays allows the surgeon to use an endoscope without having to look straight through the lens, but even more so has provided for a much greater amount of control and flexibility while conducting minimally invasive surgery.

Current state-of-the-art endoscopic surgical equipment systems are based on the integration of a series of technological improvements developed over the years. These systems include a camera head unit connected to an endoscope, a powered surgical instrument such as a shaver or an ablator, and an endoscopy cart supporting multiple smart devices including, for example, a light source unit, a camera control unit, a color printer, a patient data management device, a surgical instrument control system, a fluid management system and pump, multiple power sources, digital monitors, and several cables for power and data transmission. There are also at least two major cables connecting the endoscopy cart to the camera head unit and endoscope: one cable that transmits light from the light source through an external fiber optic light cable pathway to the endoscope, and another cable that transmits power and data signals to and from the camera head unit.

Modern endoscopic surgical procedures, which are generally considered quick and simple, actually require a lengthy preoperative period to set up the necessary equipment and require the use of a number of wires and cables that are often draped over patients and can hinder surgeons and their staff. Moreover, although state-of-the-art LED-based systems are more efficient than the older xenon lighting systems, which may use over 1000 watts of power, these newer light source units are still very power intensive, requiring 300 watts or more, most of which is wasted as heat or lost through light leaking from the external light cable. In addition, the wasted heat has been repeatedly cited as the source of operating room fires in cases where the cables were draped over a patient incorrectly or when the heated endoscope met a combustible material.

Thus, there is a need for wireless medical imaging systems that address these issues of energy efficiency, usability, versatility, and safety.

BRIEF SUMMARY OF THE INVENTION

A wireless medical imaging system is provided. The wireless medical imaging system comprises a head unit. The head unit comprises (i) a head unit case, (ii) an integrated light source, (iii) an image sensor, (iv) a wireless transceiver, (v) a central processing unit, and (vi) a user-input component. The head unit case has an external surface defining an external cavity, an internal surface defining an internal cavity, a first aperture, and a second aperture. The integrated light source, the image sensor, the wireless transceiver, and the central processing unit are disposed within the internal cavity. The integrated light source extends from within the internal cavity into the first aperture and is configured to transmit light from the head unit through the first aperture. The image sensor is configured to detect an image transmitted into the head unit through the second aperture. The external cavity is configured to receive an external battery. The user-input component is disposed on the external surface.

In one example of the wireless medical imaging system, the wireless medical imaging system further comprises an external battery. The external battery is disposed in the external cavity. The external battery provides power to one or more of the integrated light source, the image sensor, the wireless transceiver, or the central processing unit.

In another example of the wireless medical imaging system, the wireless medical imaging system further comprises a remote receiver unit. The remote receiver unit comprises a receiver unit case, a wireless transceiver, a central processing unit, and a communications interface. The receiver unit case has an internal cavity that contains the wireless transceiver of the remote receiver unit, the central processing unit of the remote receiver unit, and the communications interface.

In another example of the wireless medical imaging system, the head unit further comprises an internal rechargeable battery. The internal cavity further contains the internal rechargeable battery.

In another example of the wireless medical imaging system, the integrated light source comprises an emissive radiation source having a first spectrum, an optical element located to direct emissions from the emissive radiation source, a volumetric spectrum converter, the converter being located to convert emissions directed from the emissive radiation source to emissions having a second spectrum different from the first spectrum, an optical reflector located about the converter, and an output filter, the reflector being located to reflect the converter emissions towards the output filter. The internal cavity of the head unit case contains the emissive radiation source, the optical element, the converter, the reflector, and the filter. Desired light radiates from the internal cavity through the filter.

BRIEF DESCRIPTION OF THE DRAWINGS

Referring now to the drawings in which like reference numbers represent corresponding parts throughout.

DETAILED DESCRIPTION OF THE INVENTION

In the following description, various embodiments of a wireless medical imaging system are described. It is to be understood that other embodiments may be used and that structural changes may be made without departing from the scope of the wireless medical imaging system. Also, it is to be understood that unless otherwise indicated the wireless medical imaging system is not limited to particular materials, dimensions, manufacturing processes, or the like, as such may vary.

Figure 1:
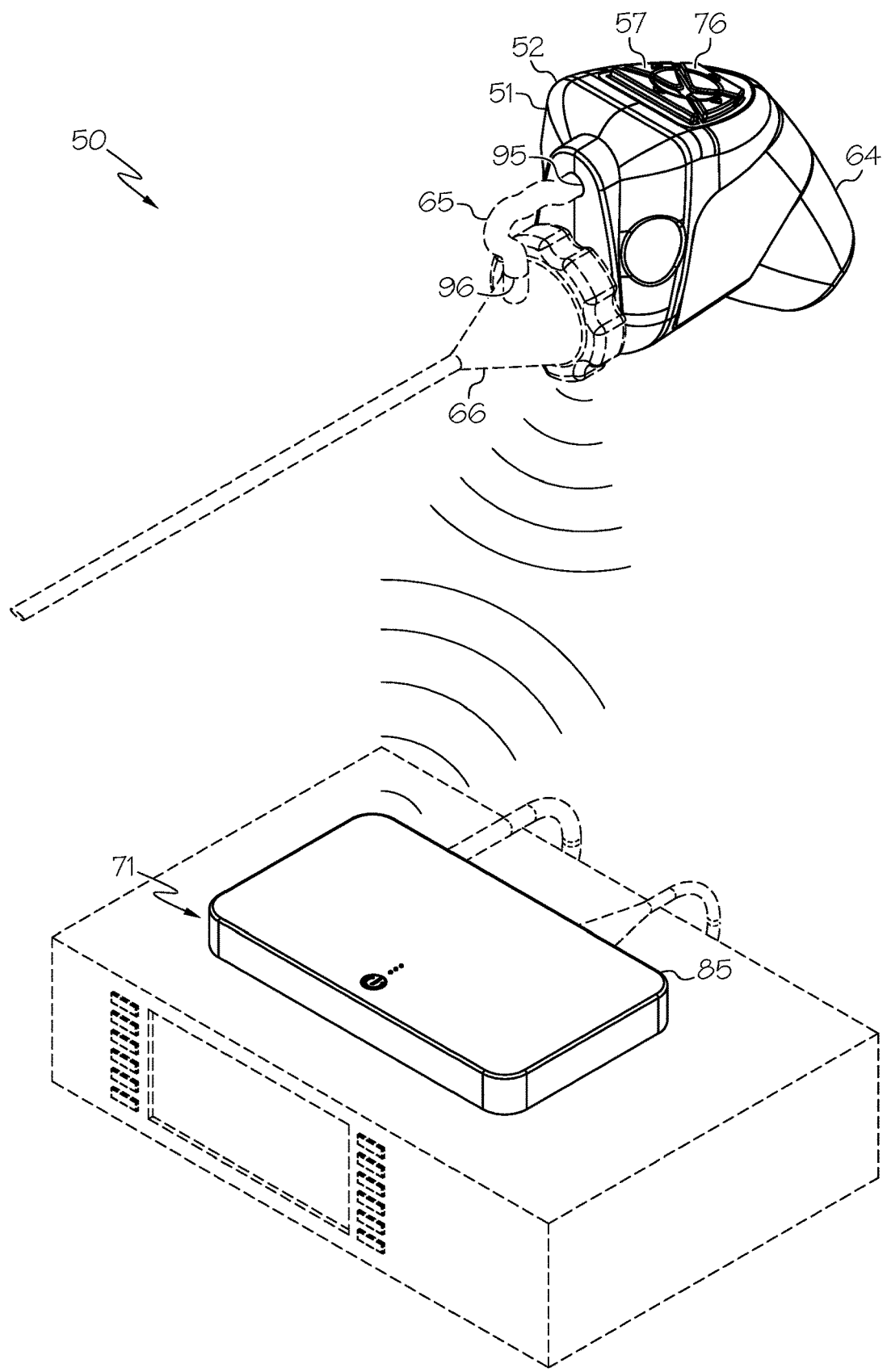
FIG. 1 shows an exemplary wireless medical imaging system of FIG. 1 as disclosed herein, in this example comprising a head unit, a removable housing comprising a removable rechargeable battery, and a remote receiver unit, wherein the removable housing comprising the removable rechargeable battery is attached to the head unit, the head unit is attached to an endoscope, and the remote receiver unit is attached to a state-of-the-art endoscopy system, in perspective view.
Figure 2:
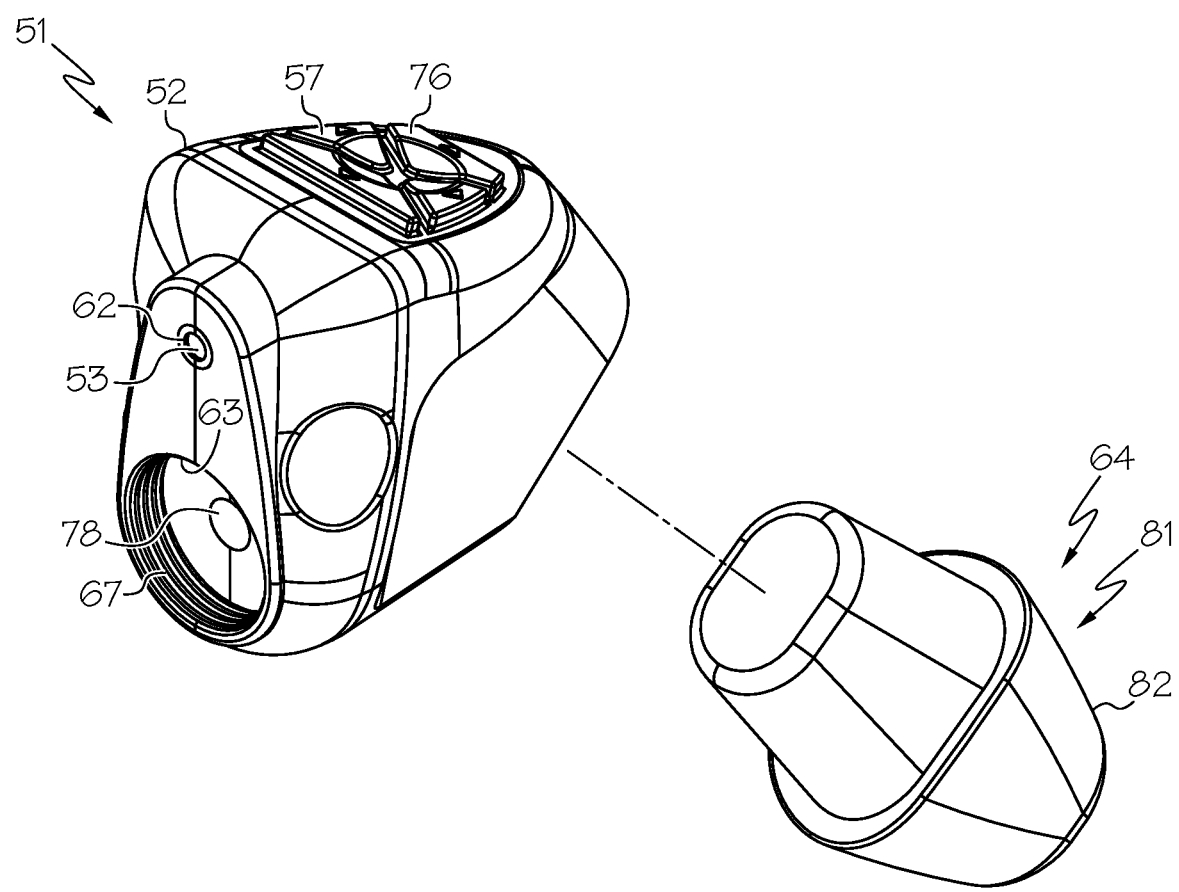
FIG. 2 shows the head unit and the removable housing comprising the removable rechargeable battery of the wireless medical imaging system of FIG. 1, in exploded view, in perspective view.
Figure 3:
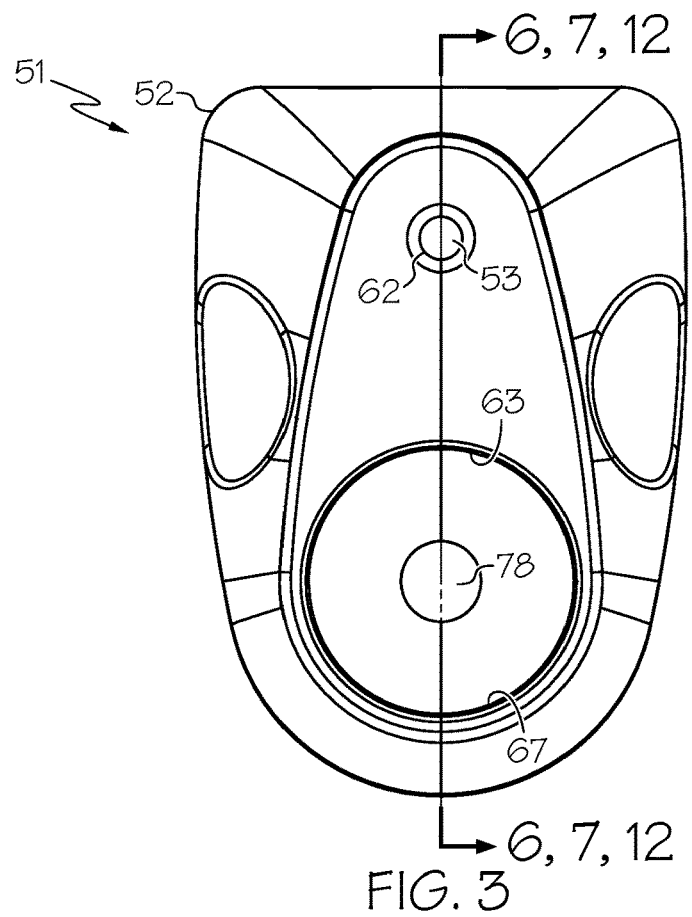
FIG. 3 shows the head unit of the exemplary wireless medical imaging system of FIG. 1, in front view.
Figure 4:
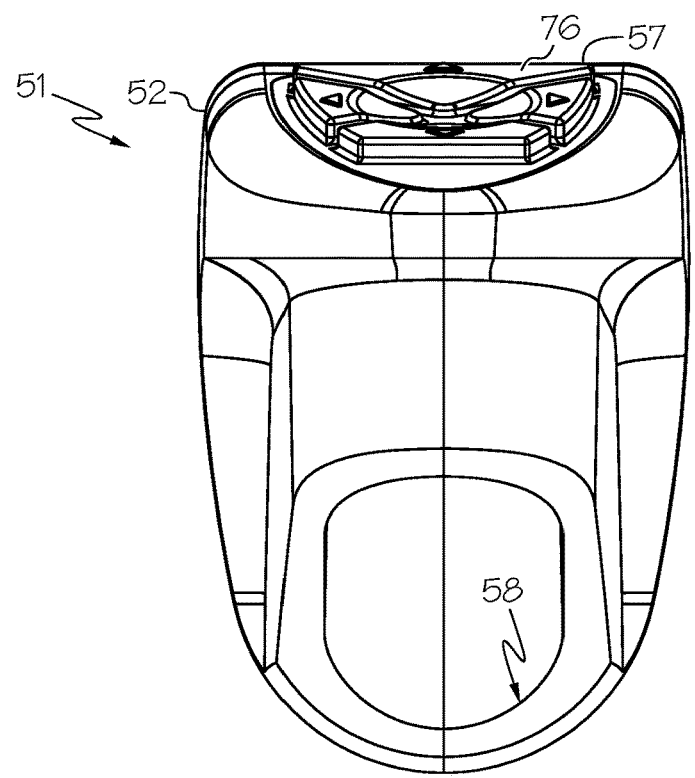
FIG. 4 shows the head unit of FIG. 3, in back view.
Figure 5:
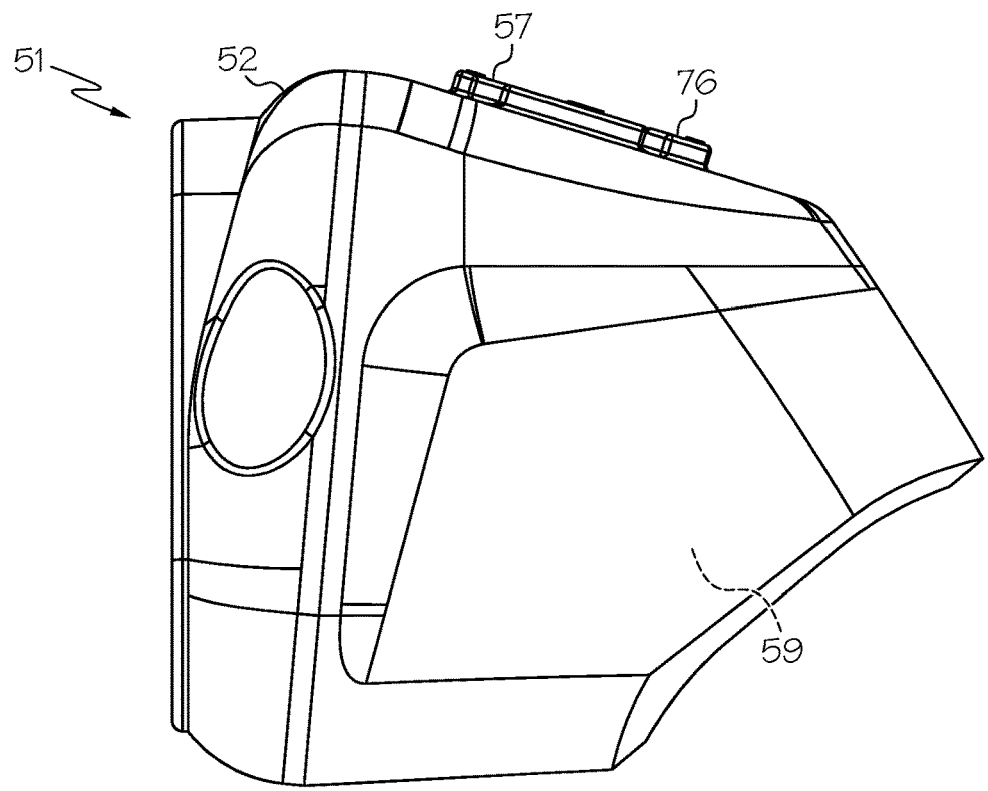
FIG. 5 shows the head unit of FIG. 3, in side view.

As shown in FIGS. 1-17, a wireless medical imaging system 50 is disclosed. As shown in FIG. 1 and FIG. 2, the wireless medical imaging system 50 comprises a head unit 51. As shown in FIGS. 3-6, the head unit 51 comprises: (i) a head unit case 52; (ii) an integrated light source 53; (iii) an image sensor 54; (iv) a wireless transceiver 55; (v) a central processing unit 56; and (vi) a user-input component 57. The head unit case 52 has an external surface 58 defining an external cavity 59, an internal surface 60 defining an internal cavity 61, a first aperture 62, and a second aperture 63. The integrated light source 53, the image sensor 54, the wireless transceiver 55, and the central processing unit 56 are disposed within the internal cavity 61. The integrated light source 53 extends from within the internal cavity 61 into the first aperture 62 and is configured to transmit light from the head unit 51 through the first aperture 62. The image sensor 54 is configured to detect an image transmitted into the head unit 51 through the second aperture 63. The external cavity 59 is configured to receive an external battery 64. The user-input component 57 is disposed on the external surface 58.

The head unit case 52 can be made by molding, casting, and/or 3D printing, among other techniques. The head unit case 52 can be made of materials such as, for example, plastic, stainless steel, and/or titanium, among others. The head unit case 52 can serve as a housing for the integrated light source 53, the image sensor 54, the wireless transceiver 55, and the central processing unit 56, for example, providing protection during use, e.g. during surgery, and during cleaning, e.g. during sterilization. With reference to FIGS. 8-12, the head unit case 52 also can serve as a structure on which the external battery 64 can be received, for example providing a site of attachment, support, and/or quick replacement of the external battery 64 during use, e.g. again during surgery.

The integrated light source 53 can be a light source for which the various components of the light source have been integrated, e.g. into a one-piece form, as opposed to, for example, a light source for which the various components remain discrete, e.g. remaining readily detachable and/or interchangeable. The integrated light source 53 can be, for example, a light emitting diode, a laser diode, or an organic light emitting diode, among other types of integrated light sources. In some examples, the integrated light source 53 comprises a solid state light source 68 that can produce continuous spectrum white light, and/or output of the integrated light source 53 has a spectral bandwidth that is nominally 480 nm to 775 nm. Also in some examples, the integrated light source 53 can produce a spectrum of light that is tunable. Also in some examples, the wireless medical imaging system 50 comprises a plurality of integrated light sources 53. Suitable examples of integrated light sources 53 are described below.

Figure 6:
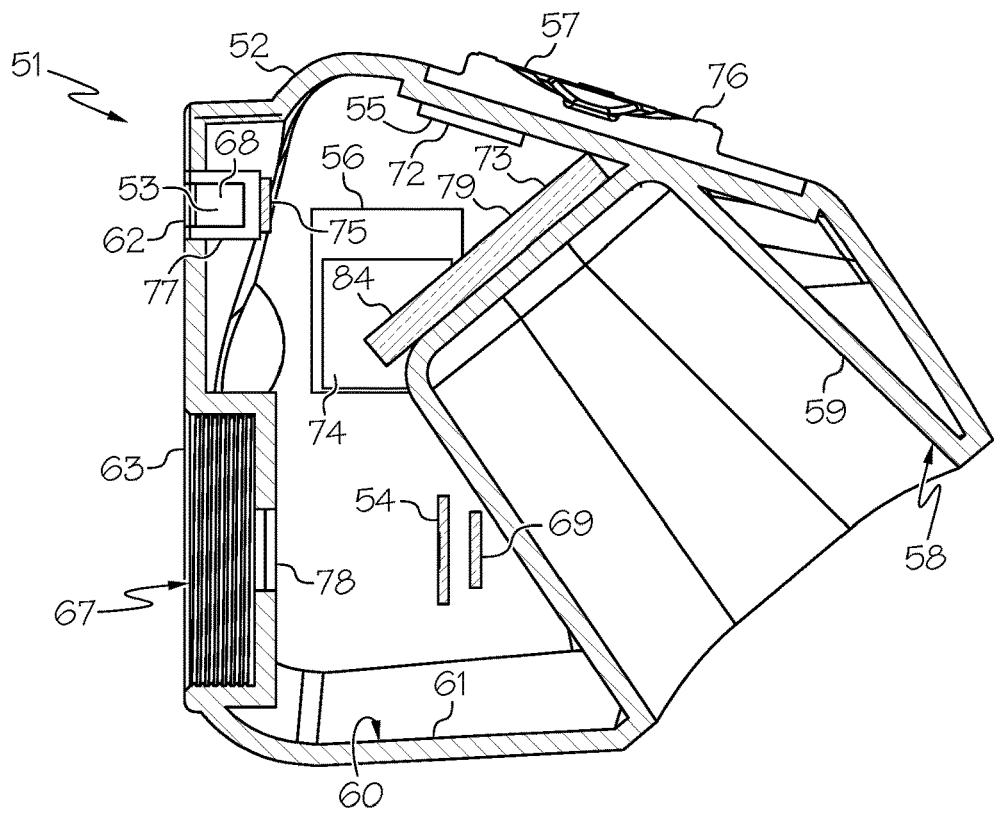
FIG. 6 shows an embodiment of the head unit of FIG. 3, in sectional view.

With reference to FIG. 1 and FIG. 6, as noted the image sensor 54 is configured to detect an image transmitted into the head unit 51 through the second aperture 63, e.g. an image transmitted by an endoscope 66 that is connected at the second aperture 63. Suitable image sensors 54 are known and commercially available, e.g. ON Semiconductor AR0230CS. In some examples, the image sensor 54 comprises a complementary metal-oxide-semiconductor (CMOS) chip, a scientific complementary metal-oxide-semiconductor (sCMOS) chip, a charge-coupled device (CCD) chip, or a combination thereof. Also in some examples, the head unit 51 further comprises a coprocessor 69 that assists the image sensor 54 in converting the image for the central processing unit 56. In these examples, the coprocessor 69 can interface with the image sensor 54. For example, the coprocessor 69 can receive input in the form of raw image data from the image sensor 54 and convert the raw image data into a format that is compressible and readable by most common image processing hardware and/or software. Suitable coprocessors 69 are known and commercially available, e.g. ON Semiconductor AP0202AT.

In some examples, the head unit case 52 has a volume of 300 to 800 $cm^3$, e.g. a volume of 350 to 750 $cm^3$, 400 to 700 $cm^3$, 450 to 650 $cm^3$, or 500 to 600 $cm^3$. Also in some examples, the integrated light source 53 and the image sensor 54 are disposed within 1 to 6 cm from each other within the head unit case 52, e.g. 1.5 to 5.5 cm, 2 to 5 cm, 2.5 to 4.5, or 3 to 4 cm from each other. Light sources conventionally used with endoscopy systems generate relatively high amounts of heat in the process of providing light to the surgical area that is bright enough for endoscopy. This generally precludes positioning such light sources in close proximity to an image sensor 54 during use, e.g. within a head unit case 52 having a volume of 300 to 800 $cm^3$, and/or within 1 to 6 cm of the image sensor 54. In contrast, as discussed below, the integrated light source 53 of the wireless medical imaging system 50 disclosed herein generates relatively low amounts of heat, while providing light output to the surgical area that is bright enough for endoscopy. This allows the integrated light source 53 to be positioned in close proximity to an image sensor 54.

With reference to FIG. 1 and FIG. 6, in some examples the head unit 51 is configured to provide illumination to an area of interest by connection of an external light cable 65. Because the head unit 51 includes the integrated light source 53, the external light cable 65 does not need to extend from an endoscopy cart, and thus can be short relative to light cables conventionally used in endoscopy. For example, the external light cable 65 can have a length of 3 to 30 cm, 4 to 20 cm, or 5 to 15 cm, among other lengths. In accordance with these examples the external light cable 65 has a first end 95 and a second end 96. The external light cable 65 can be connected to the head unit 51 at the first end 95 and to an endoscope 66 at the second end 96, such that the light is transmitted from the integrated light source 53, through the external light cable 65 and through the endoscope 66 to the area of interest. The external light cable 65 can be, for example, a reinforced light cable. Suitable external light cables 65 can be custom made from standard fiber bundles that are available from various manufacturers, or can be modified with a variety of enhancements e.g. increased durability, ease of sterilization, better light throughput, etc.

As shown in FIG. 1 and FIG. 6, in some examples the second aperture 63 comprises a connector 67 configured for connection of an endoscope 66 to the head unit case 52. The connector 67 can comprise, for example, threads, such that the second aperture 63 corresponds to a threaded cavity. Threads can allow for most common endoscopes 66 to interface correctly, either by themselves or utilizing industry standard C-Mount couplers.

As shown in FIG. 1 and FIG. 6, the wireless transceiver 55 of the head unit 51 controls and directs signals to be sent from, and received by, the wireless medical imaging system 50. As shown in FIGS. 14-17, in some examples, the wireless transceiver 55 of the head unit 51 is configured to transmit and receive image sensor 54 data, e.g. video data, and command and control signals, both to and from the wireless transceiver 70 of a remote receiver unit 71, as discussed below. In some embodiments of these examples, the head unit 51 is configured to establish a connection between the wireless transceiver 55 of the head unit 51 and the wireless transceiver 70 of the remote receiver unit 71 when the head unit 51 and the remote receiver unit 71 are located as far as 30 meters apart from each other. Also in some examples, the wireless transceiver 55 of the head unit 51 uses the ultra-wideband (UWB) communication modality. Also in some examples, the wireless transceiver 55 of the head unit 51 is configured to transmit image sensor 54 data and command and control signals to an external medical imaging system or management system without needing any changes such as reprogramming, redesign, or updates. In some examples the wireless transceiver 55 comprises and/or interfaces with an antenna 72. The antenna 72 can allow for transmitting and receiving wireless signals carrying image sensor 54 data and/or command and control signals to and from the remote receiver unit 71 and/or to and from a medical imaging system, e.g. such as a camera control unit on a standard endoscopy cart. Suitable wireless transceivers 55 are known and commercially available, e.g. Starix Technology STX1101.

With reference to FIG. 1, as noted above in some examples the head unit case 52 has a volume of 300 to 800 $cm^3$, e.g. a volume of 350 to 750 $cm^3$, 400 to 700 $cm^3$, 450 to 650 $cm^3$, or 500 to 600 $cm^3$. A head unit case 52 having a volume within these ranges can be handheld. Accordingly, the wireless transceiver 55 of the head unit 51 can transmit and receive image sensor 54 data, e.g. video data, and command and control signals, both to and from the wireless transceiver 70 of a remote receiver unit 71, with the head unit 51 being handheld.

With reference to FIG. 6, the central processing unit 56 can perform and/or control one or more functions of the wireless medical imaging system 50. In some examples, the central processing unit 56 manages at least one of the following: the integrated light source 53, the image sensor 54, or the wireless transceiver 55. In some embodiments of these examples, the central processing unit 56 can perform functions such as, for example, encoding video signals from an image sensor 54 as discussed above, decoding transmissions from the wireless transceiver 55, and/or controlling the brightness of the integrated light source 53, among others. Also in some embodiments, the central processing unit 56 can interface with a battery system 73, as discussed below, and distribute power to some or all components of the wireless medical imaging system 50, e.g. the integrated light source 53, the image sensor 54, and/or the wireless transceiver 55, among others. Also in some embodiments, the central processing unit 56 can interface with a memory module 74. The memory module 74 can allow, for example, storage and retrieval of data, instructions, and/or command signals sent by or to some or all of the components of the wireless medical imaging system 50. Also in some embodiments, the central processing unit 56 can interface with a light source driver 75. The light source driver 75 can receive power supplied by the battery system 73 as discussed below and can convert and shape the power in such a way that the integrated light source 53 can be operated efficiently. Suitable central processing units 56 are known and commercially available, e.g. NXP SCM-i.MX 6Dual.

With reference to FIG. 1 and FIG. 6, the user-input component 57 can correspond to a control surface 76 that allows a user to interface with the integrated light source 53 and/or the image sensor 54. The user-input component 57 can comprise, for example, rubber buttons, capacitive buttons, scroll wheels, capacitive screens and/or switches, which can be operatively coupled to the integrated light source 53 and/or the image sensor 54. The interfacing can comprise controlling features of the integrated light source 53, such as for example, power and/or intensity. The interfacing also can comprise controlling features of the image sensor 54, such as, for example, white balance, brightness, zoom, and/or image capture, among others.

Thus, in some examples the user-input component 57 comprises buttons configured to control functions of the integrated light source 53.

Also, in some examples the user-input component 57 comprises buttons configured to control functions of the image sensor 54.

As shown in FIG. 6, in some examples the head unit 51 further comprises a heat sink 77, the heat sink 77 being located in the internal cavity 61. The heat sink 77 can absorb heat generated by the integrated light source 53 during use. The heat sink 77 can have a variety of structures, including, for example, a heat sink/heat pipe structure. Alternatively, or additionally, the head unit case 52 itself can serve as a heat sink, e.g. a head unit case 52 made from titanium can absorb heat generated by the integrated light source 53. Suitable heat sinks 77 can be custom made to fit within head unit case 52.

Also as shown in FIG. 6, in some examples the head unit 51 further comprises a window 78. In accordance with these examples, the window 78 is disposed within the second aperture 63 and configured to allow the image to pass therethrough unimpeded. The window 78 can be made of a material such as, for example, sapphire glass, plastic, and/or acrylic, among others. The window 78 also can be covered with a coating such as, for example, an anti-reflective coating, a scratch resistant coating, and/or an infrared filtering coating, among others.

In some of these examples, the second aperture 63 comprises a connector 67 as discussed above, e.g. a connector 67 comprising threads, configured for connection of an endoscope 66 or coupler to the head unit case 52 as discussed above. In these examples, the window 78 can allow for an image transmitted by the endoscope 66 that is connected at the second aperture 63, e.g. at the second aperture 63 corresponding to a threaded hole, to pass into the head unit case 52.

Moreover, in some of these examples, the integrated light source 53, which extends from within the internal cavity 61 into the first aperture 62, and the window 78, which is disposed within the second aperture 63, effectively seal the first aperture 62 and the second aperture 63, respectively. In these examples, the integrated light source 53 is configured to transmit light from the head unit 51 through the first aperture 62, and the window 78 can allow for an image transmitted by the endoscope 66 that is connected at the second aperture 63 to pass into the head unit case 52, without compromising hermetic integrity and/or suitability for sterilization of the head unit case 52. In these examples, the head unit 51 can be sterilized prior to surgery, and the internal cavity 61 of the head unit case 52 can remain sterile during use of the head unit 51 in the surgery and thereafter.

The window 78 can be disposed within the second aperture 63 by a variety of approaches, such as, for example, by being positioned in the second aperture 63 and sealed therein.

As shown in FIG. 6, in some examples the wireless medical imaging system 50 further comprises a printed circuit board 79. The printed circuit board 79 can be disposed within the internal cavity 61 of the head unit case 52. The printed circuit board 79 can support and position one or more of the integrated light source 53, the image sensor 54, the wireless transceiver 55, and the central processing unit 56 that also are disposed within the internal cavity 61 of the head unit case 52. The printed circuit board 79 can be made of a material such as, for example, copper, plastic, fiberglass, and/or resin, among others. The printed circuit board 79 can be attached to the internal surface 60 of the head unit case 52 for stability and/or placement. Suitable printed circuit boards 79 can be custom made.

As shown in FIGS. 8-12, in some examples the wireless medical imaging system 50 further comprises an external battery 64 that is disposed in the external cavity 59 of the head unit case 52 and that provides power to one or more of the integrated light source 53, the image sensor 54, the wireless transceiver 55, or the central processing unit 56. The external battery 64 can comprise one or more battery cells 80. The battery cells 80 can have chemistries such as, for example, lithium ion, nickel cadmium, or lithium polymer, among others. Suitable battery cells 80 are known and commercially available, e.g. LG 18650MJ1.

In some embodiments of these examples, the external battery 64 is a removable rechargeable battery 81. In these embodiments, the wireless medical imaging system 50 can further comprise a removable housing 82 for the removable rechargeable battery 81. The removable housing 82 can be made of a material such as, for example, plastic, stainless steel, and/or titanium, among others. The removable housing 82 can comprise the removable rechargeable battery 81. Accordingly, the removable housing 82 can protect the removable rechargeable battery 81 during surgery and/or sterilization. The external cavity 59 can be configured to receive the removable rechargeable battery 81 via latching of the removable housing 82 into the external cavity 59. For example, the removable housing 82 can include a latch mechanism that allows for quick removal and replacement of the removable housing 82 and the removable rechargeable battery 81 therein from the external cavity 59 of the head unit case 52.

The removable housing 82 also can further comprise a battery management system 83. The battery management system 83 can perform one or more functions. For example, the battery management system 83 can be configured to (a) regulate power output from the removable rechargeable battery 81, (b) report charge level of the removable rechargeable battery 81, and (c) protect against faults. Alternatively and/or additionally, the battery management system 83 can be configured to store information identifying the removable rechargeable battery 81 such as number of charge cycles, a unique identifier, etc. Suitable battery management systems 83 can be custom made.

Figure 13:
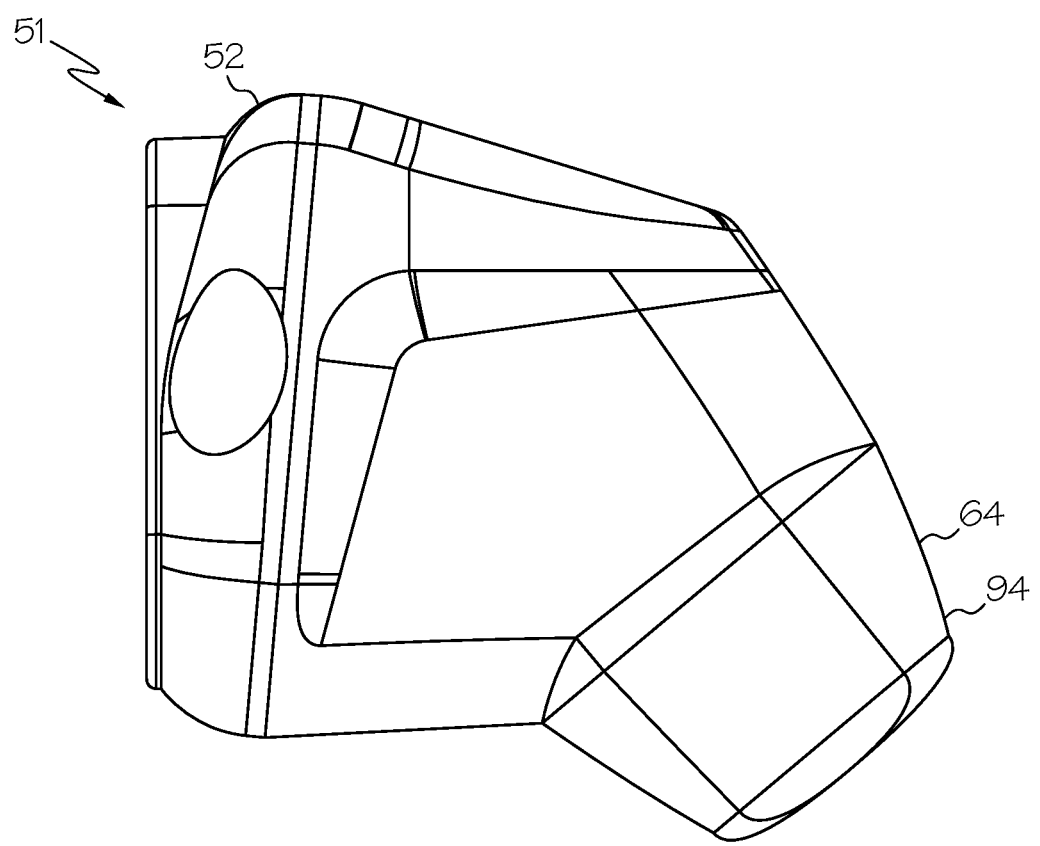
FIG. 13 shows a head unit and a non-removable rechargeable battery of an exemplary wireless medical imaging system as disclosed herein, with the non-removable rechargeable battery being attached to the head unit, in side view.
Figure 14:
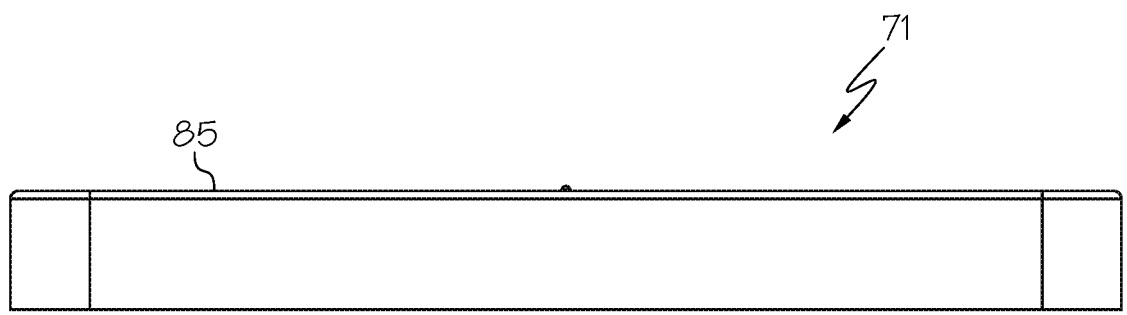
FIG. 14 shows the remote receiver unit of the exemplary wireless medical imaging system of FIG. 1, in front view.
Figure 15:
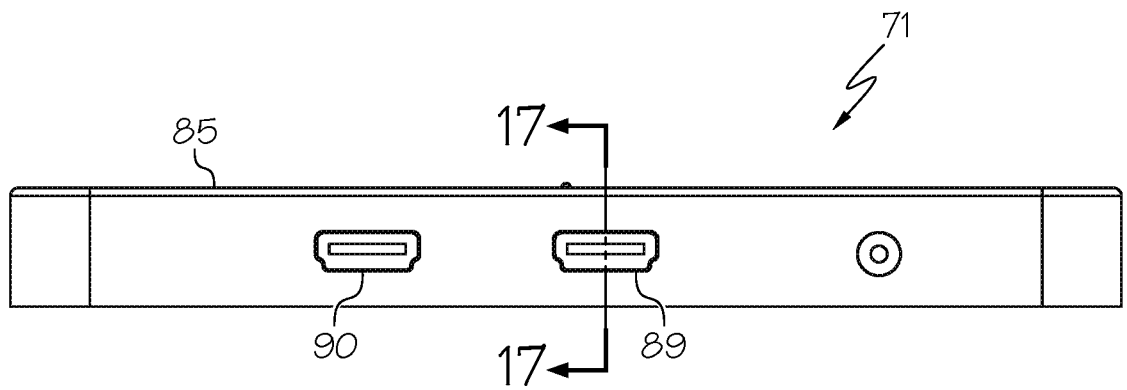
FIG. 15 shows the remote receiver unit of FIG. 14, in back view.
Figure 16:
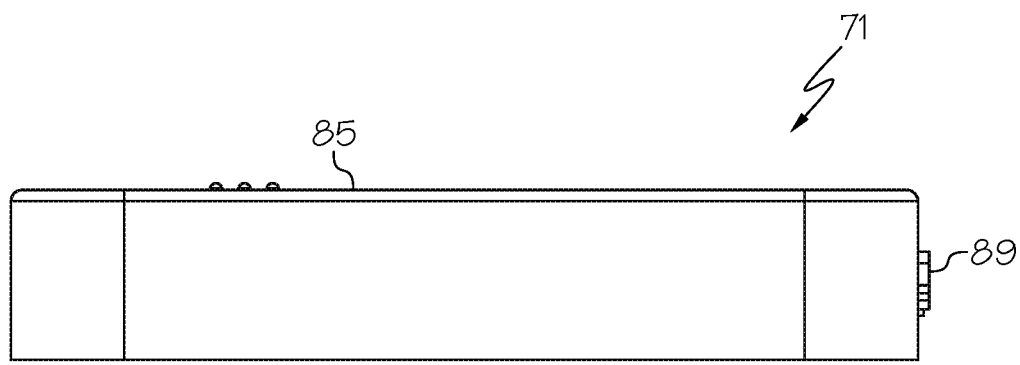
FIG. 16 shows the remote receiver unit of FIG. 14, in side view.

As shown in FIG. 13, in some embodiments of these examples, the external battery 64 is a non-removable rechargeable battery 94.

Also, returning to FIG. 6, in some embodiments of these examples, the external battery 64 has a high capacity and can provide adequate power to operate the integrated light source 53, the image sensor 54, the central processing unit 56, and the wireless transceiver 55. For example, the external battery 64 can have a capacity above 3,000 milliampere hours (mAh). Also, as noted, in some examples the wireless medical imaging system 50 comprises a plurality of integrated light sources 53. In accordance with these examples, the external battery 64 has a high capacity and can provide adequate power to operate the plurality of integrated light sources 53, as well as the image sensor 54, central processing unit 56, and the wireless transceiver 55.

Also in some embodiments of these examples, the head unit 51 further comprises a power management system 84 that is configured to control power supplied by the external battery 64 and to distribute the power to the one or more of the integrated light source 53, the image sensor 54, the wireless transceiver 55, or the central processing unit 56. Suitable power management systems 84 can be made from commercially available components, including e.g. Texas Instruments TPS63020DSJ.

As shown in FIGS. 14-17, in some examples the wireless medical imaging system 50 further comprises a remote receiver unit 71. The remote receiver unit 71 comprises a receiver unit case 85, a wireless transceiver 70, a central processing unit 86, and a communications interface 87. The receiver unit case 85 has an internal cavity 88 that contains the wireless transceiver 70 of the remote receiver unit 71, the central processing unit 86 of the remote receiver unit 71, and the communications interface 87. The remote receiver unit case 85 can be made of a material such as, for example, plastic, stainless steel, and/or titanium, among others. Accordingly, the receiver unit case 85 can protect the wireless transceiver 70 of the remote receiver unit 71, the central processing unit 86 of the remote receiver unit 71, and the communications interface, as well as any other components internal to the receiver unit case 85, e.g. in the internal cavity 88 of the receiver unit case 85, during surgery and/or cleaning.

Figure 17:
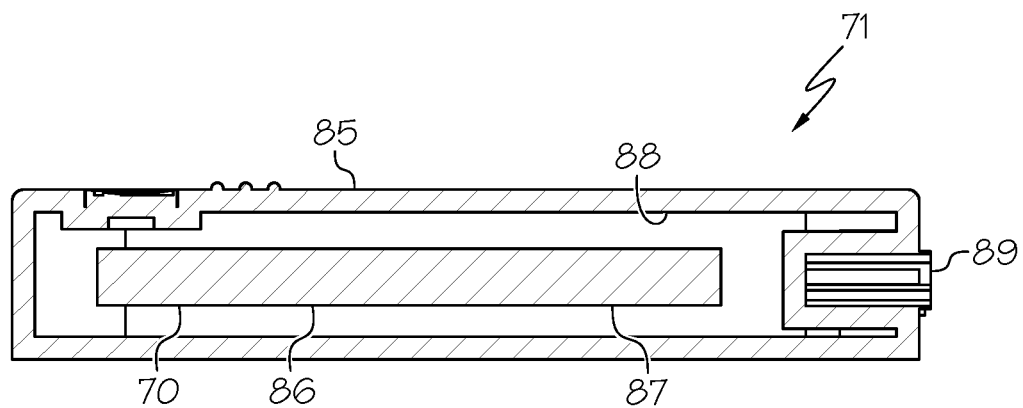
FIG. 17 shows the remote receiver unit of FIG. 15, in sectional view.

With reference to FIG. 1, FIG. 6, and FIG. 17, in some embodiments of these examples, the wireless transceiver 70 of the remote receiver unit 71 is configured to transmit and receive image sensor 54 data and command and control signals, both to and from the wireless transceiver 55 of the head unit 51. For example, the remote receiver unit 71 can include a first external connection 89 that provides connections for operations such as antenna functions, data transmission, and/or power transmission, among other operations. The remote receiver unit 71 also can include a second external connection 90 that can be used to connect the remote receiver unit 71 to an endoscopy system, including, for example, any of various existing state-of-the-art endoscopy systems.

Also in some embodiments of these examples, the central processing unit 86 of the remote receiver unit 71 manages one or more of the wireless transceiver 70 of the remote receiver unit 71 or the communications interface 87, and can perform data processing as needed. For example, the remote receiver unit 71 can comprise multiple printed circuit assemblies that can be used for functions such as, for example, power control, wireless signal processing, computation, and/or video compression and decompression, among others.

Also in some embodiments of these examples, the communications interface 87 is configured to communicate with multiple types of external camera management systems without needing any changes such as reprogramming, redesign, or updates.

Suitable wireless transceivers 70 of the remote receiver unit 71 are known and commercially available, e.g. as discussed above. Suitable central processing units 86 of the remote receiver unit 71 also are known and commercially available, e.g. as discussed above. Suitable communications interfaces 87 of the remote receiver unit 71 are known and commercially available, e.g. HDMI or DVI communications interfaces.

Figure 7:
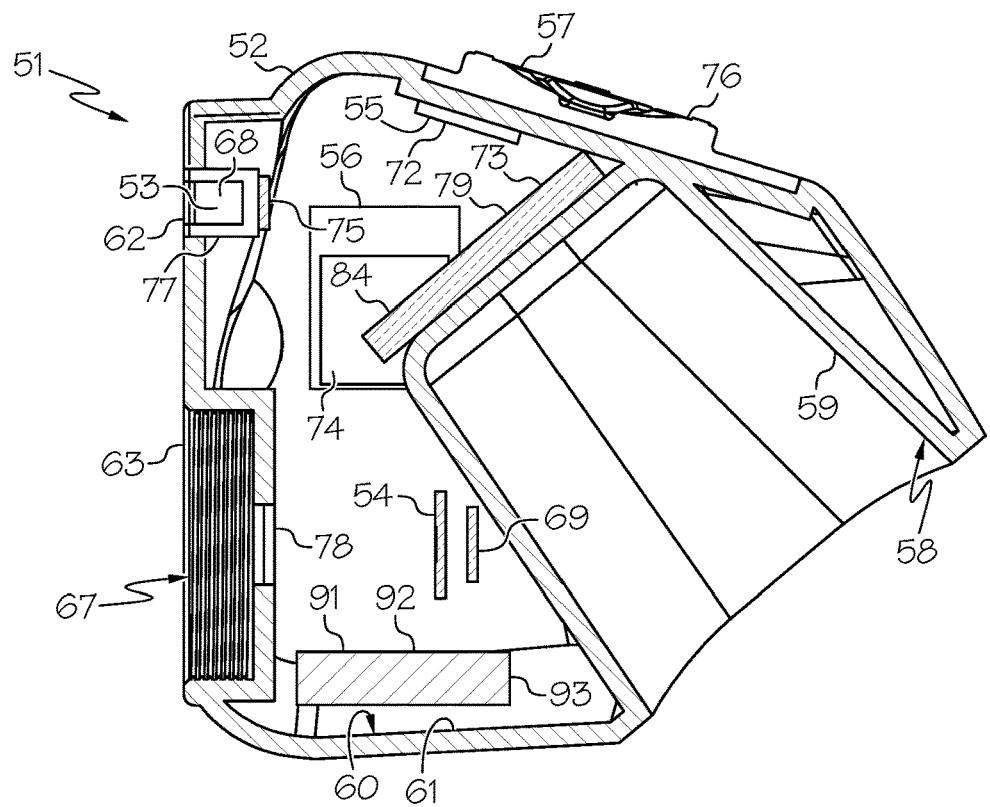
FIG. 7 shows another embodiment of the head unit of FIG. 3, wherein the head unit further comprises an internal rechargeable battery, in sectional view.
Figure 8:
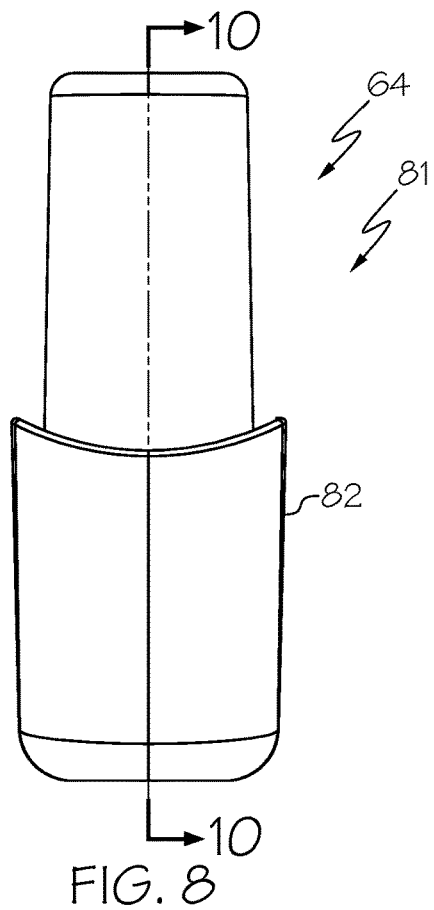
FIG. 8 shows the removable housing comprising the removable rechargeable battery of the exemplary wireless medical imaging system of FIG. 1, in front view.
Figure 9:
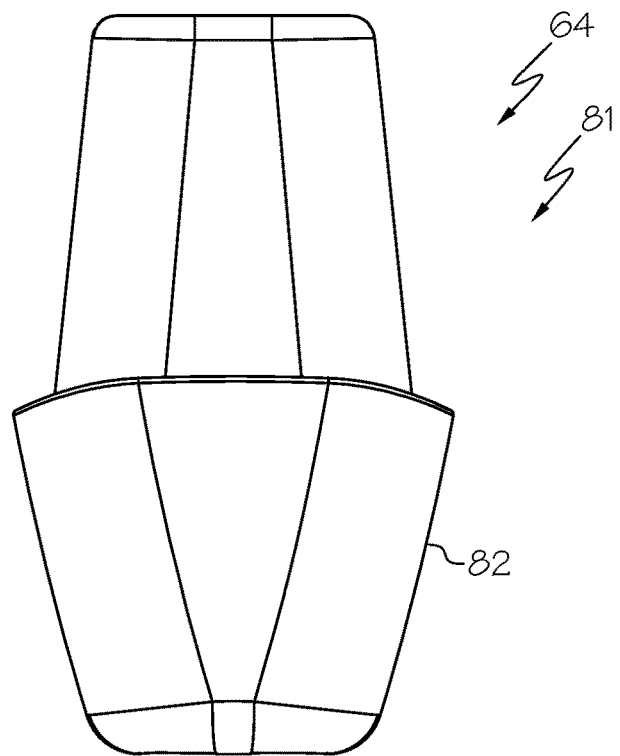
FIG. 9 shows the removable housing comprising the removable rechargeable battery of FIG. 8, in side view.
Figure 10:
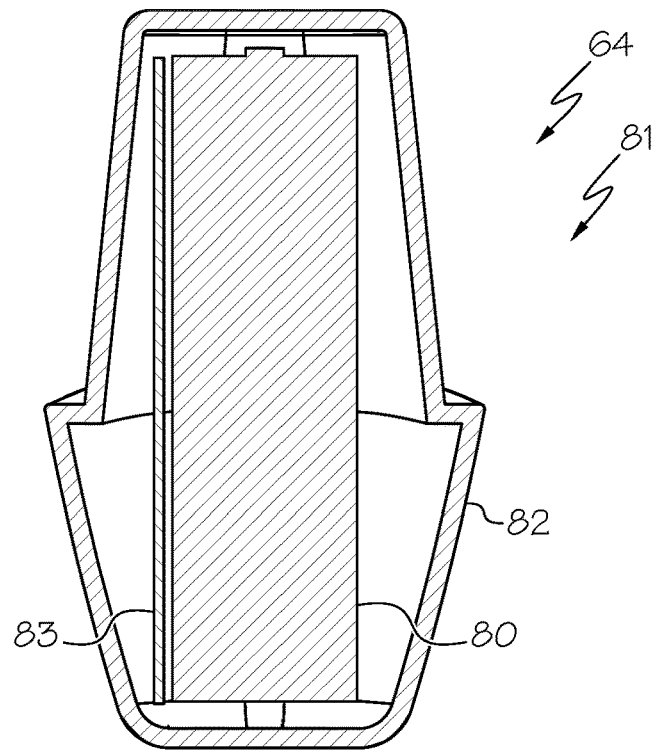
FIG. 10 shows an embodiment of the removable housing comprising the removable rechargeable battery of FIG. 8, in sectional view.
Figure 11:
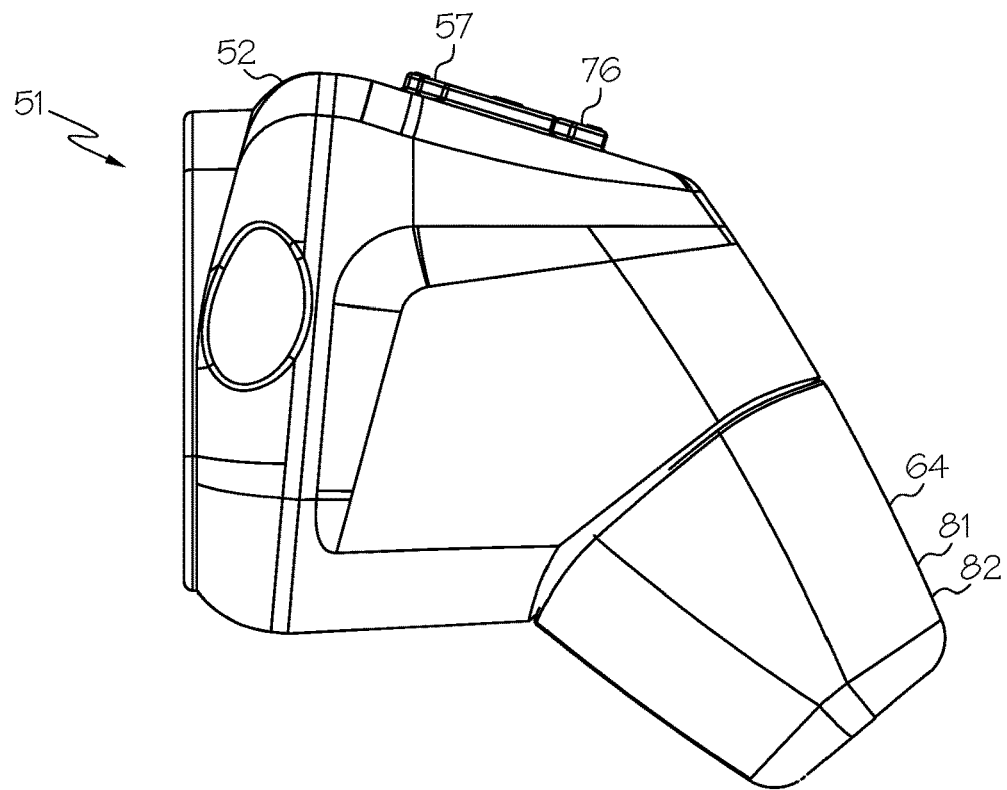
FIG. 11 shows the head unit and the removable housing comprising the removable rechargeable battery of FIG. 1, with the removable housing comprising the removable rechargeable battery being attached to the head unit, in side view.
Figure 12:
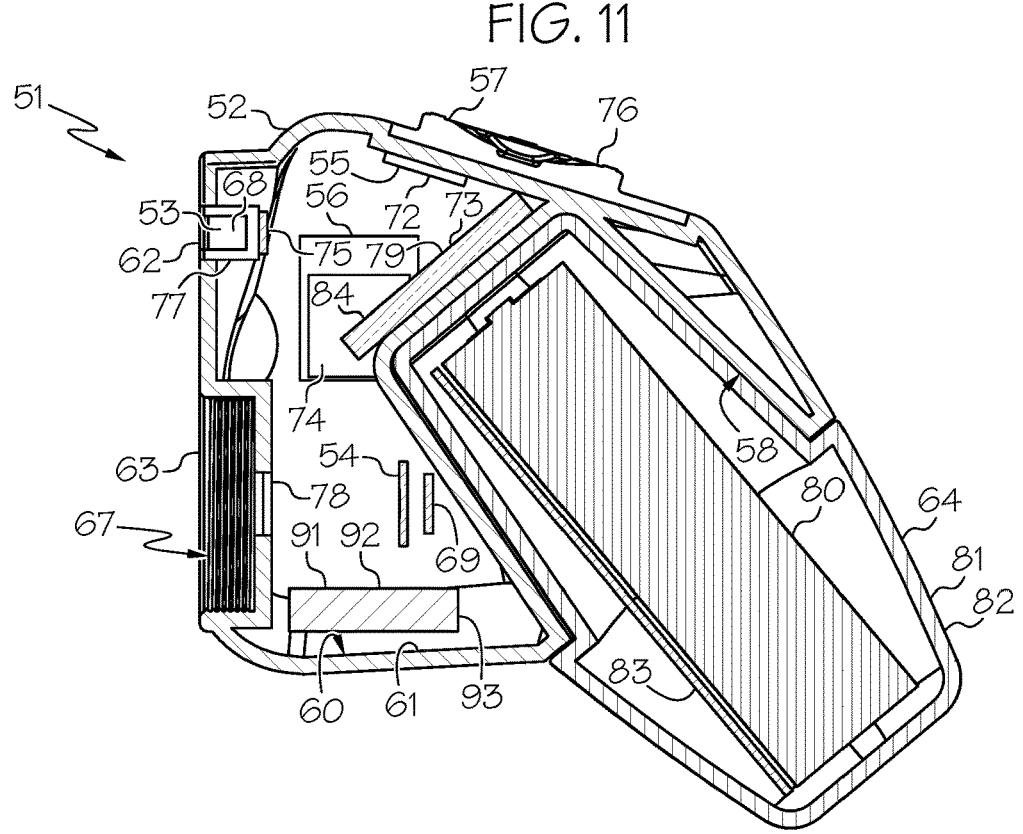
FIG. 12 shows an embodiment of the head unit of FIG. 3, with the removable housing comprising the removable rechargeable battery of FIG. 8 being attached to the head unit, in sectional view.

As shown in FIG. 7, in some examples the head unit 51 further comprises an internal rechargeable battery 91. The internal cavity 61 further contains the internal rechargeable battery 91.

In some embodiments of these examples, the internal rechargeable battery 91 is configured to be used as a secondary battery system 92 in case an external battery 64 ceases to provide power or is removed.

Also in some embodiments of these examples, the head unit 51 further comprises a battery management system 93 configured to manage the internal rechargeable battery 91. For example, the internal rechargeable battery 91 and the battery management system 93 of the head unit 51 allows for the integrated light source 53, the image sensor 54, the wireless transceiver 55, and the central processing unit 56 to switch to a lower power state in order to conserve power.

Also in some embodiments of these examples, the internal rechargeable battery 91 can be charged to capacity from an external battery 64.

Also in some embodiments of these examples, the internal rechargeable battery 91 is configured to be controlled by a separate power or battery management system 93 depending on the presence of an external battery 64.

Also in some embodiments of these examples, the internal rechargeable battery 91 is sufficient to provide power for operation of the wireless medical imaging system 50.

Suitable internal rechargeable batteries 91 are known and commercially available, e.g. as discussed above with respect to external batteries 64. Suitable battery management systems 93 also are known and commercially available, e.g. as discussed above.

With reference to FIG. 6, FIG. 7, and FIGS. 18-22, the wireless medical imaging system 50 can be used advantageously with an integrated light source 53 that provides light output that is high enough to be comparable to state-of-the-art endoscopy systems, while using less power and generating less heat than light sources conventionally used for such systems. Exemplary suitable integrated light sources 53 are as follows.

Figure 19:
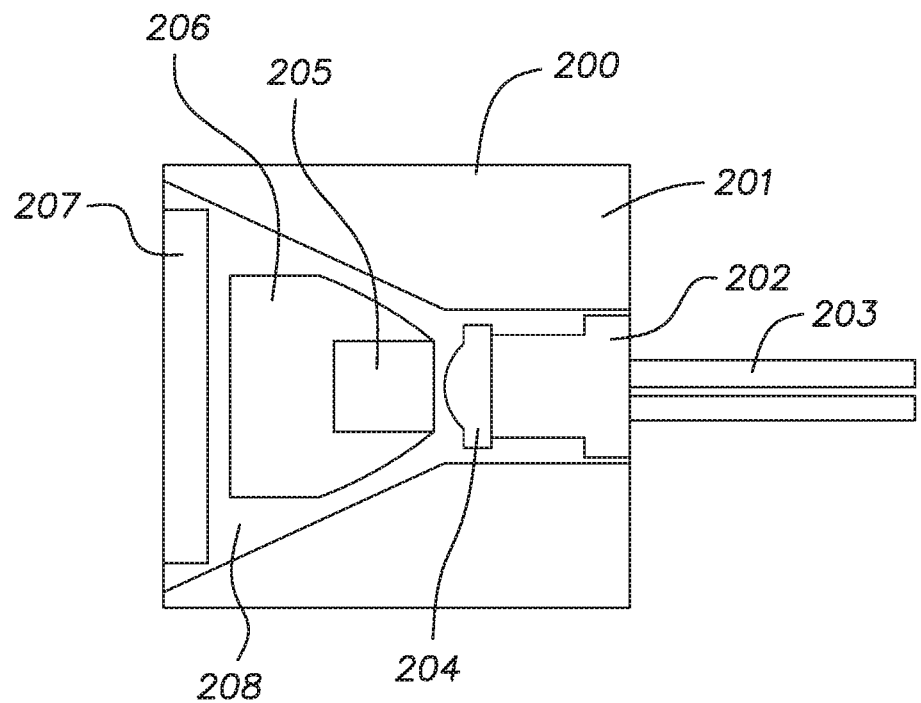
FIG. 19 is a schematic diagram of another integrated light source that uses multiple parts to enhance the efficiency and safety of the light source, as disclosed herein.

With reference to FIG. 19, and as explained in more detail below, in some examples, the integrated light source 53 is an integrated light source 200 that comprises: an emissive radiation source 202 having a first spectrum; an optical element 204 located to direct emissions from the emissive radiation source 202; a volumetric spectrum converter 205, the converter 205 being located to convert emissions directed from the emissive radiation source 202 to emissions having a second spectrum different from the first spectrum; an optical reflector 206 located about the converter 205; and an output filter 207, the reflector being located to reflect the converter emissions towards the output filter 207. In these examples, the internal cavity 61 of the head unit case 52 as discussed above contains the emissive radiation source 202, the optical element 204, the converter 205, the reflector 206, and the filter 207. Desired light radiates from the internal cavity 61 through the filter 207.

In some embodiments of these examples, the emissive radiation source 202 operates in the range of 400 nm to 480 nm. The optical element 204 may either collimate, convergently focus, or divergently focus the emissive radiation source emissions onto the converter 205. The optical reflector 206 redirects omnidirectional light into a desired optical path. The converter 205 converts the emissions from the emissive radiation source 202 to emissions of different wavelength, a narrower spectrum, or a broader spectrum, of non-coherent radiation. The filter 207 eliminates an emission from the emissive radiation source 202 that has not been converted by the converter 205 as well as optionally further conditioning the emitted light. The emissive geometry of the emitted radiation spectrum from the integrated light source 200 may be further conditioned, directed, focused, collimated, reflected, refracted, diffracted, or otherwise modified with the inclusion of suitable optical components.

The light source 200 employs a solid state light emitting device pumping a medium wherein phosphor is volumetrically disposed. The light emitting device produces a beam of light that is directed onto the phosphor and subsequently converted into either a broad- or narrow-spectrum light of desired wavelengths. By using a volumetrically disposed phosphor, a higher percentage of the incoming light can be converted, thus increasing the efficiency and safety of the system. This converted light can then be sent over a desired optical path so as to control the final light output precisely.

The light source is based on a method for volumetrically disposing phosphorescent materials into a substrate. A volumetrically disposed substrate provides benefits over, for example, a current system of using a thin coating. One benefit is increased conversion of laser light into non-coherent light, which stems from the amount of phosphor available for light conversion. The current thin surface coatings of phosphor get saturated with pre-converted light quickly and can only convert a small amount of light at a time, greatly decreasing system efficiency. Attempting to increase the amount of light-converting phosphor using the current thin surface coatings of phosphor becomes extremely difficult as coherent light only travels in one direction, and thus requires the layer of phosphor to either increase in thickness, which impedes transmission and therefore effectiveness, or be distributed across a prohibitively large area. Using a volumetric deposition method allows for a larger amount of phosphor to be used in converting coherent light, without creating the need for a larger emission beam of the coherent light. An increase in the amount of phosphor being used for conversion means that more non-coherent light is produced with the same input; therefore the system is more efficient. In addition, as more coherent light is converted to non-coherent light, there is a decline in possibility that there will be dangerous coherent laser light emanating from the final light source system.

Figure 18:
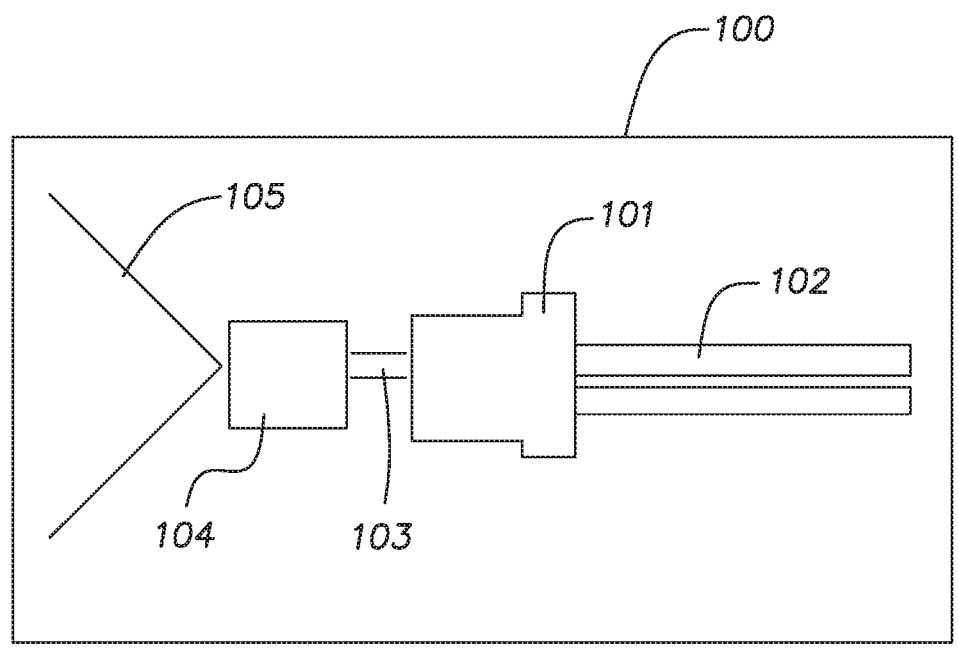
FIG. 18 is a schematic diagram of a basic solid state integrated light source as disclosed herein.

Considering exemplary suitable light sources 53 in more detail, referring to FIG. 18, an exemplary solid state integrated light source 100 is illustrated. The integrated light source 100 includes a laser diode 101 in the form of a semiconductor laser disposed inside of a standard electronics component package. The laser diode 101 has power pins 102 exiting the package. The laser diode 101 may, for example, provide coherent light within the range of 400-480 nm and, preferably, 430-470 nm. Beam 103 is the coherent beam of laser light that the laser diode 101 produces. Beam 103 strikes, and interacts with, volumetric spectrum converter 104 (e.g., PMMA, which is volumetrically disposed with particles of phosphor). Converter 104 thusly converts the incoming coherent laser beam 103 into outgoing broad spectrum light 105. The light 105 may be of any specified color, such as, but not limited to, white, and is decided by the chemical composition of the phosphor disposed in the medium of the converter 104.

Referring to FIG. 19, another exemplary integrated light source 200 is illustrated. The integrated light source 200 includes an emissive radiation source 202 having a first output spectrum, for example, in the form of a semiconductor laser diode disposed inside of a standard electronics component package. The laser diode has power pins 203 exiting the package. Situated in front of the emission side of the emissive radiation source 202 is an optical element 204 composed, for example, of a lens, or system of lenses, that directs the coherent laser light emitted from the laser diode 202 onto a specific area. The optical element 204 may, for example, collimate, convergently focus, or divergently focus the emissions of the emissive radiation source 202 for conversion by the volumetric spectrum converter 205. The volumetric spectrum converter 205 converts the emissions from the emissive radiation source 202 to emissions having a second spectrum different than the first spectrum. The volumetric spectrum converter 205 is disposed inside of a geometric optical reflector 206 which is in this embodiment, but is not limited to, a parabolic solid that directs the light converted by the converter 205 towards a specified direction, which, in this case, is forward towards an output filter 207. After the light has been directed forward by the optical reflector 206, the light interacts with the filter 207 which removes any coherent light that has not been converted into non-coherent light by the converting medium of the converter 205. Following this, only the filtered, non-coherent light can exit the light source 200 making the emitted light safe to use in multiple environments. Referring to the light source 200, all aforementioned components are situated in an internal cavity 208 which is excised from a package body 201, which may be, for example, a piece of solid material such as, but not limited to, aluminum, steel, or copper.

Figure 20:
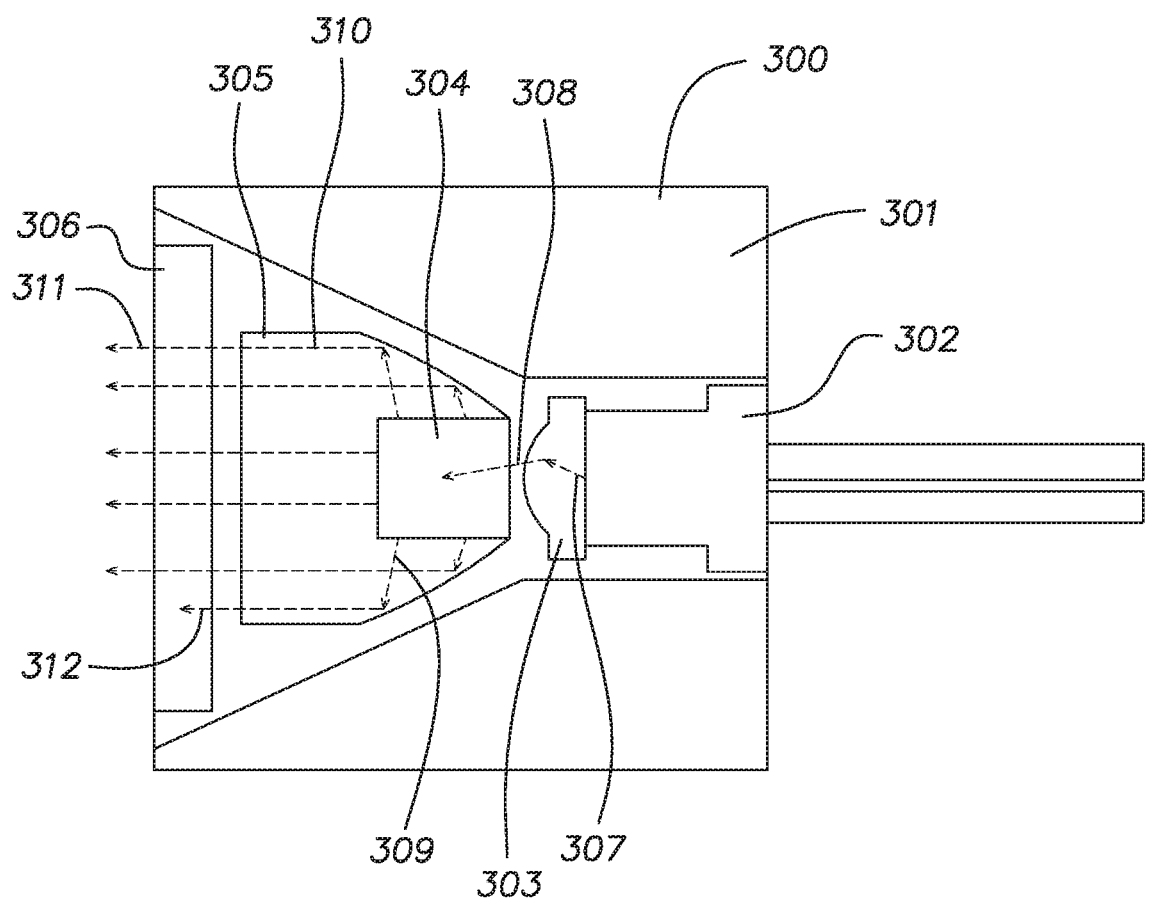
FIG. 20 is a schematic diagram that uses the integrated light source of FIG. 19 and illustrates a possible beam path for the light in the system.

Referring to FIG. 20, a possible light path using the light source seen in FIG. 19 is illustrated. The light source 300, which is comparable to the light source 200 of FIG. 19, includes a package body 301, which is comparable to package body 201 of FIG. 19. Within the light source 300 is positioned a laser diode 302 in the form of a semiconductor laser disposed inside of a standard electronics component package. The laser diode 302 emits a beam of coherent light 307, which proceeds to interact with optical element 303. The optical element 303 redirects the coherent beam 307 into a more precise path 308, which allows it to interact more efficiently with the volumetric spectrum converter 304. The converter 304 converts the coherent light 308 into non-coherent light 309 through internal physical interaction between the coherent light 308 with the volumetrically disposed phosphor present in the converter 304. Subsequently the non-coherent light 309 is emitted in multiple directions from the converter 304. The non-coherent light 309 then interacts with the geometric optical reflector 305. This optical reflector 305 reflects the non-coherent multi-directional light 309 and redirects it forward 310. Most of the redirected light 310 passes through the filter 306 and leaves 311 the light source 300. Some of the redirected light 310 interacts with the filter 306 and is prevented 312 from exiting the device for reasons such as design and safety specifications.

Figure 21:
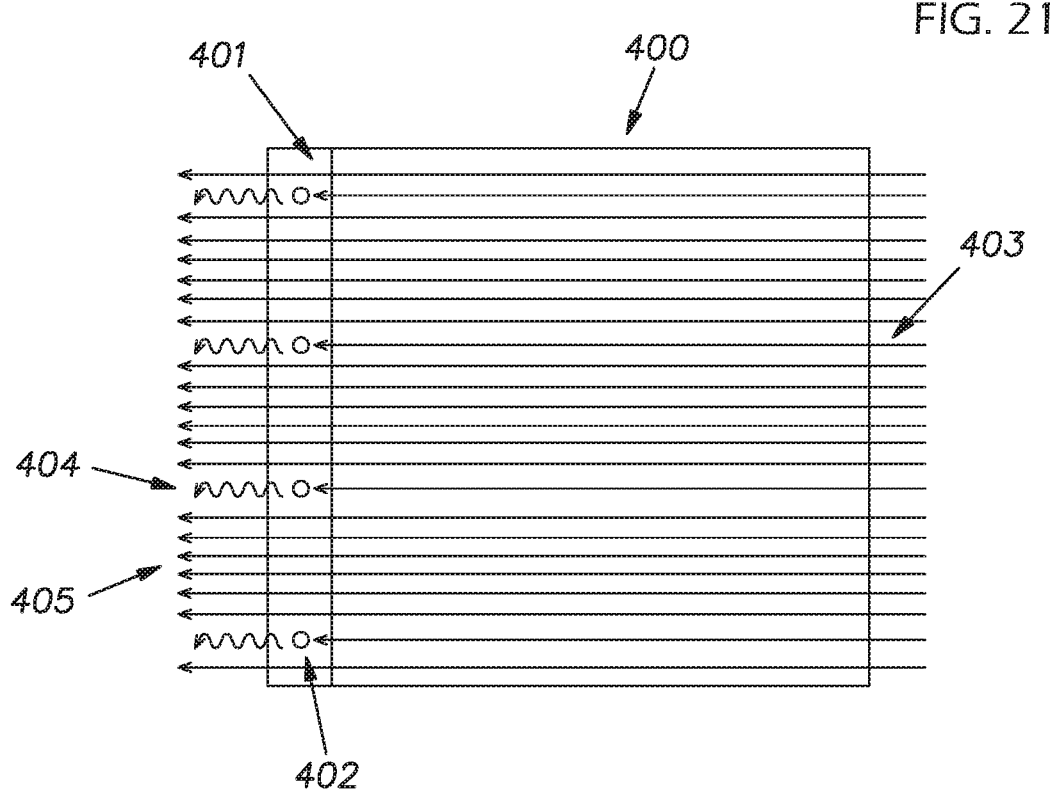
FIG. 21 is a schematic diagram of the operation of a phosphor coated converter.

FIG. 21 illustrates a phosphor coated converter. The portion 401 is a thinly deposited phosphor coating on a substrate 400. The thin phosphor coating 401 has particles of phosphor 402 that are disposed within the coating. The particles 402 convert light coming in from the right side 403 into a different wavelength of light 404. Because the coating layer 401 is thin, there is a limited amount of phosphor particles 402 that can convert the incoming light 403. Therefore, a large portion of the incoming light 403 is not converted, and leaves the substrate unaffected 405.

Figure 22:
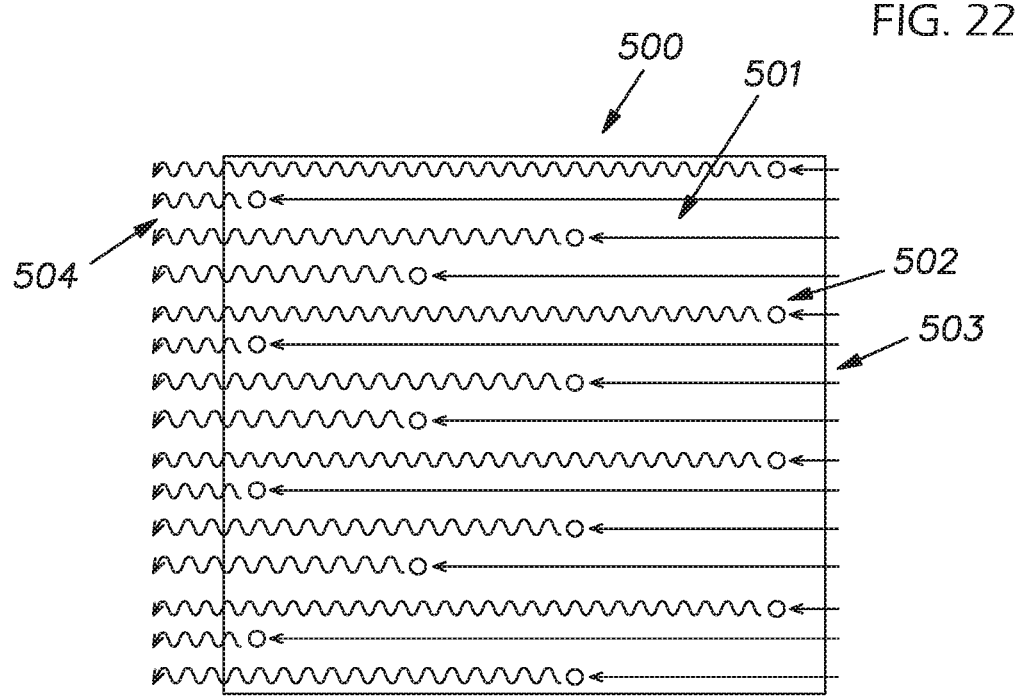
FIG. 22 is a schematic diagram of the operation of an example volumetric spectrum converter according to an aspect of the integrated light source disclosed herein.

FIG. 22 illustrates a volumetric spectrum converter, as opposed to the coating in FIG. 21. In this case, the phosphor 501 is volumetrically disposed within the substrate 500. This leads to more particles of phosphor 502 that can interact with the incoming light 503, and therefore participate in light conversion. Here there is a much larger amount of incoming light 503 that gets converted into the desired wavelength 504. The use of a volumetric spectrum converter outperforms phosphor coated converters.

It should be noted that this is a simplification for clarity. The emitted light does not necessarily come out of the front all together. It is generally scattered omnidirectionally, and the reflective paraboloid (e.g., 206, 305) of the light source is what makes the light go in the same direction.

The optical reflector may be, for example, a molded, machined, 3-D printed or otherwise fabricated piece of optical material such as PMMA, polystyrene, polycarbonate, polyester, copolymers or blends of a combination of the aforementioned materials. It is designed to redirect omnidirectional light into a desired optical path. It may be, for example, a solid geometric form, a hollow geometric form, or other combinations of geometric surfaces. It may also advantageously include a layer of reflective material that enhances its capacity to redirect light. This layer may be, for example, an external surface, an internal surface, or a combination of surfaces.

The converter (e.g., 205, 304) may be chosen to convert emissions from the emissive radiation source (e.g., blue or violet light) to radiation of another wavelength, for example, narrow or broad spectrum, non-coherent radiation. It may be made using converting material that may include, for example, phosphorescent material, florescent material, other radiation converting material, or combinations of these materials. The converting material is volumetrically disposed in a substrate that may include, for example, PMMA, polystyrene, polycarbonate, polyester, copolymers or blends of a combination of the aforementioned materials to create an effectively homogenous composite. This process may include, for example, extrusion, coating, lamination, blending, mixing, or suspending.

A particular example of making a converter is extruding a substrate with the converting material as a blended and/or multilayered solid composite. In particular, the solid composite can be made with between 2 and 500,000 layers which can be tuned for specified end use performance metrics. It is desirable for the converter to not have any defects, such as, for example, voids, entrapped gas, air bubbles, adulterating particulate of any material other the those purposely desired, or entrapped liquid of any sort, either vapor or liquid state, larger than 1 micron.

The converter can possess a ratio of converting material, or a combination of multiple materials to the substrate, that can be tuned for specified end use performance metrics.

In a preferred embodiment, the converting material may be of a single phosphor with a particular particulate size, or a mix of phosphor powders with either similar or dissimilar particulate sizes providing an emission of radiation that is either of a stable and/or variable wavelength. The emitted radiation can be for example, white light.

In another preferred embodiment, the converter possesses a ratio of converting material to the substrate between 5% and 15%.

It is also possible to tune the converter for specified end use performance metrics by varying the thickness and diameter of the converter. For example, a preferred embodiment includes a converter with a thickness of between 0.5 mm and 5 mm and a radius of between 0.5 mm and 5 mm.

With reference to FIG. 6, FIG. 19, and FIG. 20, the output filter (e.g., 207, 306) may be, for example, an optically clear window 78, but in the preferred embodiment, it eliminates any emitted radiation from the emissive radiation source that has not been converted by the converter. It also may be, for example, a long-pass, short-pass, band-pass or band-stop filter to further pass or cutoff wavelengths of radiation, to further condition the emitted light.

It should be further noted that the emissive geometry of the emitted radiation spectrum from the device may be further conditioned, directed, focused, collimated, reflected, refracted, diffracted, or otherwise modified with the inclusion of suitable optical components.

Figure 23:
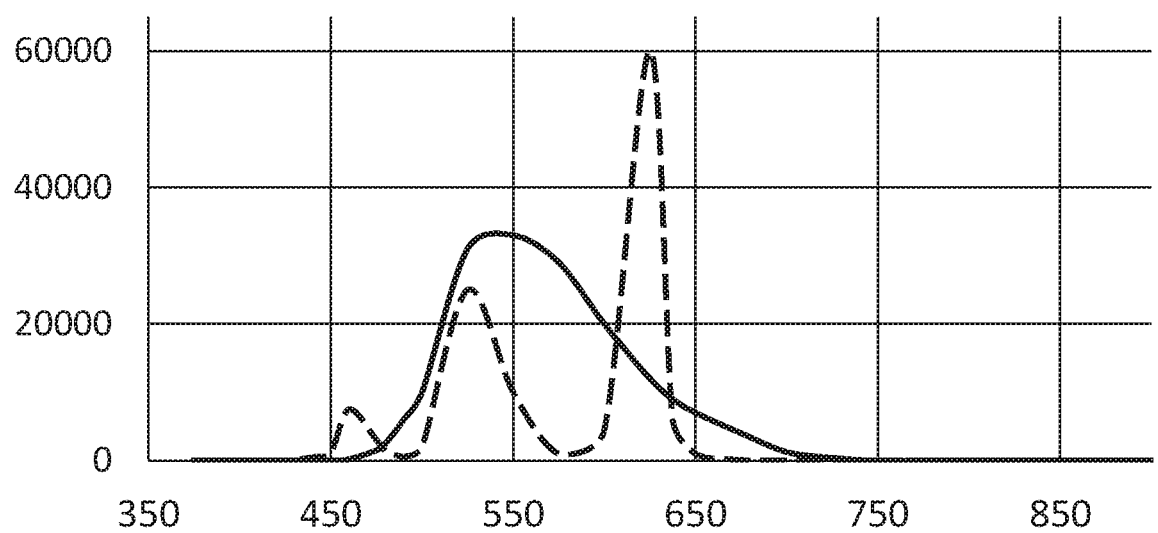
FIG. 23 is a graph comparing exemplary spectra (Y-axis: intensity; X-axis: wavelength (nm)) of a state-of-the-art 3-LED system (dashed line) and an integrated light source as disclosed herein (solid line).

Importantly, the light source as disclosed herein can be used to provide a continuous sun-light equivalent spectrum that is useful for both the human eye and modern camera systems, while at the same time providing a total light intensity that is equivalent to that of current systems at a lower power requirement. For example, as shown in FIG. 23, which is a graph comparing exemplary spectra of a state-of-the-art 3-LED system (dashed line) and an integrated light source as disclosed herein (solid line), current systems such as the state-of-the-art 3-LED system have three peaks corresponding to the three LED colors used. While the human eye can add these together and perceive a decent approximation of white light, modern camera systems are more sensitive and may exhibit deficiencies where there are gaps in a spectrum. By providing a continuous sun-light equivalent spectrum, the light source as disclosed herein overcomes such deficiencies, and does so while providing an equivalent total light intensity (integrals of both graphs are similar) at a lower power requirement.

The wireless medical imaging system disclosed herein provides many advantages, including the following.

The wireless medical imaging system eliminates the need for the many cables associated with conventional endoscopy systems. The wireless medical imaging system can provide an internal light source, a removable and hot-swappable battery system, and an FCC-compliant, FDA-approved, and HIPAA-compliant wireless modality for data transmission. The wireless medical imaging system can be integrated easily, even drop-in compatible, to current endoscopy systems, surgical workflows, and operating rooms.

The external battery, which can be in the form of a battery pack, can be made of a sufficient number of cells that, when fully charged, can last through the average length of a complete surgery. without needing to be changed. Also, if the battery pack is not fully charged before a surgery, or if a surgery takes longer than the battery charge lasts, then the battery pack can be hot-swapped with minimal disruption to the surgery performance and time.

The integrated light source can be of a range of modalities, providing light output that is bright enough to be comparable to state-of-the-art endoscopy systems, and small enough to be disposed inside the head unit of the wireless medical imaging system. This eliminates the need for a long external light transfer cable extending from an endoscopy cart, and the associated need to compensate for the amount of light lost through the external light cable. This in turn allows for the light source to provide an amount of light to surgical areas that are comparable, or even greater than, the amount of light provided by state-of-the-art endoscopy systems, while using less power and emitting less waste heat. In addition, the absence of a long light transfer cable allows surgeons to have a much higher degree of flexibility in manipulating an endoscope. This eliminates the tripping hazard that an external light cable creates, and provides for much easier and more comprehensive sterilization. The integrated light source also generates less heat, decreasing the possibility that materials in the operating room will catch fire from hot cables and/or other hot/radiative components.

State-of-the-art image sensors, having increased low-light sensitivity, decreased power requirements, increased resolution, and a number of improvements with regard to smart features such as automatic white balancing, automatic exposure, and automatic tone correction, can be used. This allows for a further reduction in the light output required from the integrated light source to adequately illuminate the surgical area without diminishing image quality, thus making the system more energy efficient, while still providing clear and workable images to surgeons.

The head unit can be operated without a data cable attached thereto. State-of-the-art endoscopy systems use a data cable to transfer images from a camera head unit to a camera control unit located on an endoscopy cart. While this data cable is usually thinner and more flexible than an external light cable, this data cable presents the same problems of motion restriction, tripping concerns, and sterilization difficulty. The medical imaging system described above includes a wireless transmission modality that can transfer the large amount of data needed for latency free, real-time video and command and control signals in a way that is compliant with relevant laws and regulations. While there are many wireless transmission modalities that have the capability to transfer the amount of data at the speed required, there are very few that are FDA or FCC approved for use in an operating room. Likewise, of the modalities that are approved for use in the operating room, most lack the necessary bandwidth to accomplish the transmission task, e.g. transfer of 1080p or higher video data at a minimum of 30 frames per second. For the few modalities that are both approved for use in an operating room and that have an appropriate bandwidth capacity to transfer video data within required performance parameters, it is believed that none had been used previously for duplex transmission between a surgical device to a monitor or controller, as disclosed herein.

The wireless medical imaging system can also be designed to be drop-in compatible with other endoscopy systems that are most commonly used, thus allowing easy adoption of the wireless medical imaging system in operating rooms.

These improvements should result in reduced setup times for operating rooms, increased safety within operating rooms, simplified, yet more efficacious, sterilization, and improved usability and flexibility for surgeons during procedures. In combination, these advances should allow for shorter and safer surgeries, improve patient outcomes, and reduce risk and costs to hospitals and surgical centers.

The following are exemplary embodiments of the wireless medical imaging system.

Embodiment 1

A wireless medical imaging system comprising a head unit, the head unit comprising: (i) a head unit case; (ii) an integrated light source; (iii) an image sensor; (iv) a wireless transceiver; (v) a central processing unit; and (vi) a user-input component; wherein: the head unit case has an external surface defining an external cavity, an internal surface defining an internal cavity, a first aperture, and a second aperture; the integrated light source, the image sensor, the wireless transceiver, and the central processing unit are disposed within the internal cavity; the integrated light source extends from within the internal cavity into the first aperture and is configured to transmit light from the head unit through the first aperture; the image sensor is configured to detect an image transmitted into the head unit through the second aperture; the external cavity is configured to receive an external battery; and the user-input component is disposed on the external surface.

Embodiment 2

The wireless medical imaging system according to embodiment 1, wherein: the integrated light source comprises a solid state light source that can produce continuous spectrum white light; and/or output of the integrated light source has a spectral bandwidth that is nominally 480 nm to 775 nm.

Embodiment 3

The wireless medical imaging system according to embodiment 1 or 2, wherein the head unit is configured to provide illumination to an area of interest by connection of an external light cable, the external light cable having a first end and a second end, the external light cable being connected to the head unit at the first end and to an endoscope at the second end, such that the light is transmitted from the integrated light source, through the external light cable and the endoscope, to the area of interest.

Embodiment 4

The wireless medical imaging system according to any of embodiments 1-3, wherein the image sensor comprises a complementary metal-oxide-semiconductor (CMOS) chip, a scientific complementary metal-oxide-semiconductor (sCMOS) chip, a charge-coupled device (CCD) chip, or a combination thereof.

Embodiment 5

The wireless medical imaging system according to any of embodiments 1-4, wherein the wireless transceiver of the head unit is configured to transmit and receive image sensor data and command and control signals, both to and from a wireless transceiver of a remote receiver unit.

Embodiment 6

The wireless medical imaging system according to embodiment 5, wherein the head unit is configured to establish a connection between the wireless transceiver of the head unit and the wireless transceiver of the remote receiver unit when the head unit and the remote receiver unit are located as far as 30 meters from each other.

Embodiment 7

The wireless medical imaging system according to any of embodiments 1-6, wherein the wireless transceiver of the head unit uses the ultra-wideband (UWB) communication modality.

Embodiment 8

The wireless medical imaging system according to any of embodiments 1-7, wherein the wireless transceiver of the head unit is configured to transmit data from the image sensor and command and control signals to an external system for management of medical imaging systems without need for reprogramming or redesign.

Embodiment 9

The wireless medical imaging system according to any of embodiments 1-8, wherein the central processing unit manages at least one of the integrated light source, the image sensor, or the wireless transceiver.

Embodiment 10

The wireless medical imaging system according to any of embodiments 1-9, wherein the head unit further comprises a coprocessor that assists the image sensor in converting the image for the central processing unit.

Embodiment 11

The wireless medical imaging system according to any of embodiments 1-10, wherein the user-input component comprises buttons configured to control functions of the image sensor.

Embodiment 12

The wireless medical imaging system according to any of embodiments 1-11, wherein the second aperture comprises a connector configured for connection of an endoscope to the head unit case.

Embodiment 13

The wireless medical imaging system according to any of embodiments 1-12, wherein the head unit case has a volume of 300 to 800 cm$^3$.

Embodiment 14

The wireless medical imaging system according to any of embodiments 1-13, wherein the integrated light source and the image sensor are disposed within 1 to 6 cm from each other.

Embodiment 15

The wireless medical imaging system according to any of embodiments 1-14, wherein the head unit further comprises a heat sink, the heat sink being located in the internal cavity.

Embodiment 16

The wireless medical imaging system according to any of embodiments 1-15, wherein the head unit further comprises a window, the window being disposed within the second aperture and configured to allow the image to pass therethrough.

Embodiment 17

The wireless medical imaging system according to any of embodiments 1-16, wherein the wireless medical imaging system further comprises an external battery that is disposed in the external cavity and that provides power to one or more of the integrated light source, the image sensor, the wireless transceiver, or the central processing unit.

Embodiment 18

The wireless medical imaging system according to embodiment 17, wherein the external battery is a removable rechargeable battery.

Embodiment 19

The wireless medical imaging system according to embodiment 18, wherein the wireless medical imaging system further comprises a removable housing for the removable rechargeable battery, the removable housing comprising the removable rechargeable battery, and the external cavity being configured to receive the removable rechargeable battery via latching of the removable housing into the external cavity.

Embodiment 20

The wireless medical imaging system according to embodiment 19, wherein the removable housing further comprises a battery management system.

Embodiment 21

The wireless medical imaging system according to embodiment 20, wherein the battery management system is configured to (a) regulate power output from the removable rechargeable battery, (b) report charge level of the removable rechargeable battery, and (c) protect against faults.

Embodiment 22

The wireless medical imaging system according to embodiment 17, wherein the external battery is a non-removable rechargeable battery.

Embodiment 23

The wireless medical imaging system according to embodiment 17, wherein the external battery has a high capacity and can provide adequate power to operate the integrated light source, the image sensor, and the wireless transceiver.

Embodiment 24

The wireless medical imaging system according to embodiment 23, wherein the external battery has a capacity above 3,000 milliampere hours (mAh).

Embodiment 25

The wireless medical imaging system according to embodiment 17, wherein the head unit further comprises a power management system that is configured to control power supplied by the external battery and to distribute the power to the one or more of the integrated light source, the image sensor, the wireless transceiver, or the central processing unit.

Embodiment 26

The wireless medical imaging system according to any of embodiments 1-25, wherein the wireless medical imaging system further comprises a remote receiver unit, the remote receiver unit comprising: a receiver unit case; a wireless transceiver; a central processing unit; and a communications interface; wherein the receiver unit case has an internal cavity that contains the wireless transceiver of the remote receiver unit, the central processing unit of the remote receiver unit, and the communications interface.

Embodiment 27

The wireless medical imaging system according to embodiment 26, wherein the wireless transceiver of the remote receiver unit is configured to transmit and receive image sensor data and command and control signals, both to and from the wireless transceiver of the head unit.

Embodiment 28

The wireless medical imaging system according to embodiment 26 or 27, wherein the central processing unit of the remote receiver unit manages one or more of the wireless transceiver of the remote receiver unit or the communications interface and can perform data processing therefor.

Embodiment 29

The wireless medical imaging system according to any of embodiments 26-28, wherein the communications interface is configured to communicate with multiple types of external camera management systems without need for reprogramming or redesign.

Embodiment 30

The wireless medical imaging system according to any of embodiments 1-29, wherein the head unit further comprises an internal rechargeable battery, the internal cavity further containing the internal rechargeable battery.

Embodiment 31

The wireless medical imaging system according to embodiment 30, wherein the internal rechargeable battery is configured to be used as a secondary battery system in case an external battery ceases to provide power or is disconnected.

Embodiment 32

The wireless medical imaging system according to embodiment 30 or 31, wherein the head unit further comprises a battery management system configured to manage the internal rechargeable battery.

Embodiment 33

The wireless medical imaging system according to embodiment 32, wherein the internal rechargeable battery and the battery management system of the head unit allow the integrated light source, the image sensor, the wireless transceiver, and the central processing unit to switch to a lower power mode in order to conserve power.

Embodiment 34

The wireless medical imaging system according to any of embodiments 30-33, wherein the internal rechargeable battery can be charged to capacity from an external battery.

Embodiment 35

The wireless medical imaging system according to any of embodiments 30-34, wherein the internal rechargeable battery is configured to be controlled externally by a separate power or battery management system depending on the presence of an external battery.

Embodiment 36

The wireless medical imaging system according to any of embodiments 30-35, wherein the internal rechargeable battery is sufficient to provide power for operation of the wireless medical imaging system.

Embodiment 37

The wireless medical imaging system according to any of embodiments 1-36, wherein the integrated light source comprises: an emissive radiation source having a first spectrum; an optical element located to direct emissions from the emissive radiation source; a volumetric spectrum converter, the converter being located to convert emissions directed from the emissive radiation source to emissions having a second spectrum different from the first spectrum; an optical reflector located about the converter; and an output filter, the reflector being located to reflect the converter emissions towards the output filter; wherein the internal cavity of the head unit case contains the emissive radiation source, the optical element, the converter, the reflector, and the filter, and wherein desired light radiates from the internal cavity through the filter.

Embodiment 38

The wireless medical imaging system according to embodiment 37, wherein the emissive radiation source operates in the range of 400 nm to 480 nm.

Embodiment 39

The wireless medical imaging system according to embodiment 37 or 38, wherein the optical element may either collimate, convergently focus, or divergently focus the emissive radiation source emissions onto the converter.

Embodiment 40

The wireless medical imaging system according to any of embodiments 37-39, wherein the optical reflector redirects omnidirectional light into a desired optical path.

Embodiment 41

The wireless medical imaging system according to any of embodiments 37-40, wherein the converter converts the emissions from the emissive radiation source to emissions of different wavelength, a narrower spectrum, or a broader spectrum, of non-coherent radiation.

Embodiment 42

The wireless medical imaging system according to any of embodiments 37-41, wherein the filter eliminates an emission from the emissive radiation source that has not been converted by the converter as well as optionally further conditioning the emitted light.

Embodiment 43

The wireless medical imaging system according to any of embodiments 37-42, wherein the emissive geometry of the emitted radiation spectrum from the integrated light source may be further conditioned, directed, focused, collimated, reflected, refracted, diffracted, or otherwise modified with the inclusion of suitable optical components.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

The invention claimed is:

1. A wireless medical imaging system comprising:
   a head unit including a head unit case having an external surface defining an external cavity and an internal surface defining an internal cavity, the external surface having a substantially planar front face, and a first aperture and a second aperture extending through the front face such that the first aperture is generally co-planar with the second aperture, wherein the second aperture is configured to receive an endoscope such that the endoscope extends from the front face;
   an integrated light source optically coupled to the first aperture and comprising:
      an emissive radiation source emitting a first spectrum of radiation; and
      a volumetric spectrum converter being located to convert the first spectrum of radiation directed from the emissive radiation source to a second spectrum of radiation different from the first spectrum of radiation,
      wherein the head unit includes an external cable coupling the first aperture to the endoscope and the integrated light source is coupled to an end of the external cable such that light emitted from the integrated light source is transmitted from the integrated light source through the endoscope to an area of interest;
   an image sensor disposed within the head unit and configured to detect an image transmitted into the head unit through the second aperture;
   a wireless transceiver and a central processing unit disposed within the internal cavity of the head unit; and
   a user-input component disposed on the external surface of the head unit.

2. The wireless medical imaging system according to claim 1, wherein the emissive radiation source operates in a range of 400 nm to 480 nm.

3. The wireless medical imaging system according to claim 1, wherein the integrated light source further comprises:
   an optical element located to direct the first spectrum of radiation from the emissive radiation source;
   an optical reflector located about the volumetric spectrum converter; and
   an output filter, the optical reflector being located to reflect the second spectrum of radiation from the volumetric spectrum converter towards the output filter,
   wherein the emissive radiation source, optical element, volumetric spectrum converter, reflector, and output filter are contained within the internal cavity and desired light radiates from the internal cavity through the output filter.

4. The wireless medical imaging system according to claim 3, wherein the optical element may either collimate, convergently focus, or divergently focus the first spectrum of radiation from the emissive radiation source onto the volumetric spectrum converter.

5. The wireless medical imaging system according to claim 3, wherein the optical reflector redirects omnidirectional light into a desired optical path.

6. The wireless medical imaging system according to claim 3, wherein the output filter eliminates any of the first spectrum of radiation from the emissive radiation source that has not been converted by the volumetric spectrum converter as well as optionally further conditioning the second spectrum of radiation.

7. The wireless medical imaging system according to claim 1, wherein the volumetric spectrum converter converts the first spectrum of radiation from the emissive radiation source to emissions of different wavelengths, a narrower spectrum, or a broader spectrum, of non-coherent radiation.

8. The wireless medical imaging system according to claim 1, wherein an emissive geometry of the emissions of the second spectrum may be further conditioned, directed, focused, collimated, reflected, refracted, diffracted, or otherwise modified with an inclusion of suitable optical components.

9. The wireless medical imaging system according to claim 1, wherein:
   the integrated light source comprises a solid state light source that can produce continuous spectrum white light; and/or
   output of the integrated light source has a spectral bandwidth that is nominally 480 nm to 775 nm.

10. The wireless medical imaging system according to claim 1, wherein the wireless transceiver of the head unit may use ultra-wideband (UWB) communication modality.

11. The wireless medical imaging system according to claim 1, wherein the central processing unit manages at least one of the integrated light source, the image sensor, or the wireless transceiver.

12. The wireless medical imaging system according to claim 1, wherein the second aperture comprises a connector configured for connection of the endoscope to the head unit case.

13. The wireless medical imaging system according to claim 12, wherein the connector is a C-mount coupler.

14. The wireless medical imaging system according to claim 1, wherein the head unit further comprises a window, the window being disposed within the second aperture and configured to allow the image to pass therethrough.

15. The wireless medical imaging system according to claim 1, wherein an external battery is disposed in the external cavity and provides power to one or more of the integrated light source, the image sensor, the wireless transceiver, or the central processing unit.

16. The wireless medical imaging system according to claim 15, wherein the external battery is a removable rechargeable battery.

17. The wireless medical imaging system according to claim 16, wherein the wireless medical imaging system further comprises a removable housing for the removable rechargeable battery, the removable housing comprising the removable rechargeable battery, and the external cavity being configured to receive the removable rechargeable battery via latching of the removable housing into the external cavity.

18. The wireless medical imaging system according to claim 15, wherein an exposed surface of the external battery is flush with the external surface of the head unit when the external battery is disposed within the external cavity, the exposed surface including a curved portion.

19. The wireless medical imaging system according to claim 1, wherein the wireless medical imaging system further comprises a remote receiver unit, the remote receiver unit comprising:
   a receiver unit case;
   a wireless transceiver;
   a central processing unit; and
   a communications interface,
   wherein the receiver unit case has an internal cavity that contains the wireless transceiver of the remote receiver unit, the central processing unit of the remote receiver unit, and the communications interface.

20. The wireless medical imaging system according to claim 1, wherein the first aperture is adjacent to the second aperture.

21. The wireless medical imaging system according to claim 1, wherein the first aperture is disposed on an imaginary plane and the second aperture is disposed on the imaginary plane.

22. The wireless medical imaging system according to claim 1, wherein the second aperture is threaded.

23. The wireless medical imaging system according to claim 21, wherein the integrated light source does not extend distally past the imaginary plane.

24. The wireless medical imaging system according to claim 1, wherein an external battery extends away from the head unit.

25. The wireless medical imaging system according to claim 1, wherein an external battery is disposed within a housing received by the external cavity, the housing configured to be coupled to the external surface.

26. The wireless medical imaging system according to claim 1, wherein the integrated light source, the image sensor, the wireless transceiver, and the central processing unit are disposed within the internal cavity.

27. The wireless medical imaging system according to claim 1, wherein the external cavity is configured to receive an external battery.

28. The wireless medical imaging system according to claim 1, wherein the volumetric spectrum converter includes one or more phosphors, each with a particular particulate size providing an emission of radiation that is of a stable or variable wavelength.

29. The wireless medical imaging system according to claim 1, wherein the emissive radiation source is a laser.

30. The wireless medical imaging system according to claim 1, wherein the volumetric spectrum converter does not have any defects including voids, entrapped gas, air bubbles, adulterating particulate of any material other than those purposely desired, or entrapped liquid of any sort, either vapor or liquid state, larger than 1 micron.

31. The wireless medical imaging system according to claim 1, wherein the integrated light source extends at least partially through the first aperture proximate the front face.

32. The wireless medical imaging system according to claim 1, wherein the integrated light source is coupled to the first aperture proximate the front face.

33. The wireless medical imaging system according to claim 1, wherein the head unit includes an imaginary plane extending along the front face, the first aperture and the second aperture being disposed on the imaginary plane such that a first axis extending through the first aperture and a second axis extending through the second aperture are substantially parallel to each other.

34. The wireless medical imaging system according to claim 33, wherein the first axis and the second axis are substantially perpendicular to the plane.

35. The wireless medical imaging system according to claim 1, wherein the volumetric spectrum converter includes a homogeneous composite substrate with a plurality of suspended particles disposed throughout the homogeneous composite substrate, each of the plurality of suspended particles being configured to convert the first spectrum of radiation to the second spectrum of radiation.

36. The wireless medical imaging system according to claim 35, wherein the volumetric spectrum converter possesses a ratio of converting material to the homogeneous composite substrate between 5% and 15% by volume.

37. The wireless medical imaging system according to claim 35 wherein a plurality of layers is combined to form the homogeneous composite substrate such that the homogenous composite substrate is a single volumetrically monolithic structure.

38. The wireless medical imaging system according to claim 1, wherein the user-input component comprises at least one button configured to control one or more functions of one or more of the image sensor and the integrated light source.

39. The wireless medical imaging system according to claim 1, wherein the user-input component is disposed on a top surface of the head unit, the top surface being generally perpendicular to the planar front face.

40. The wireless medical imaging system according to claim 39, wherein the user-input component is disposed on the top surface proximate the wireless transceiver.

41. A wireless medical imaging system comprising:
a head unit comprising:
a head unit case having an external surface defining an external cavity and an internal surface defining an internal cavity, the external surface having a first aperture and a second aperture;
an integrated light source optically coupled to the first aperture, the integrated light source comprising:
an emissive radiation source emitting a first spectrum of radiation; and
a volumetric spectrum converter being located to convert the first spectrum of radiation directed from the emissive radiation source to a second spectrum of radiation different from the first spectrum of radiation, the volumetric spectrum converter including a homogeneous composite substrate with a plurality of suspended particles disposed throughout the homogeneous composite substrate, each of the plurality of suspended particles being configured to convert the first spectrum of radiation to the second spectrum of radiation, wherein the homogenous composite substrate is comprised of poly(methyl methacrylate) (PMMA);
an image sensor configured to detect an image transmitted into the head unit through the second aperture;
a wireless transceiver and a central processing unit disposed within the internal cavity of the head unit; and
a user-input component disposed on the external surface.

42. A wireless medical imaging system comprising:
a head unit comprising:
a head unit case having an external surface defining an external cavity and an internal surface defining an internal cavity, the external surface having a first aperture and a second aperture;
an integrated light source optically coupled to the first aperture, the integrated light source comprising:
an emissive radiation source emitting a first spectrum of radiation; and
a volumetric spectrum converter being located to convert the first spectrum of radiation directed from the emissive radiation source to a second spectrum of radiation different from the first spectrum of radiation, the volumetric spectrum converter including a homogeneous composite substrate with a plurality of suspended particles disposed throughout the homogeneous composite substrate, each of the plurality of suspended particles being configured to convert the first spectrum of radiation to the second spectrum of radiation, wherein a length of the homogeneous composite substrate is substantially the same as a width of the homogeneous composite substrate, the length being along a direction of the light coming from the head unit and the width being perpendicular to the length;
an image sensor configured to detect an image transmitted into the head unit through the second aperture;
a wireless transceiver and a central processing unit disposed within the internal cavity of the head unit; and
a user-input component disposed on the external surface.

* * * * *